US008454989B2

(12) United States Patent
Lee et al.

(10) Patent No.: US 8,454,989 B2
(45) Date of Patent: *Jun. 4, 2013

(54) LAMINATED INGESTIBLE DOSAGE FORM FOR DISPENSING MULTIPLE BIOACTIVE SUBSTANCES

(75) Inventors: Brian Craig Lee, Corvallis, OR (US); Steven W. Steinfield, San Diego, CA (US); Winthrop D. Childers, San Diego, CA (US); Mark A. Van Veen, Cardiff by the Sea, CA (US); Mohammad M. Samii, La Jolla, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 2392 days.

This patent is subject to a terminal disclaimer.

(21) Appl. No.: 11/111,240

(22) Filed: Apr. 20, 2005

(65) Prior Publication Data
US 2005/0186253 A1      Aug. 25, 2005

Related U.S. Application Data

(63) Continuation of application No. 10/028,450, filed on Oct. 24, 2001, now Pat. No. 6,962,715.

(51) Int. Cl.
*A61K 47/00* (2006.01)
*A61K 9/68* (2006.01)
*A61K 9/28* (2006.01)
*A61K 9/14* (2006.01)

(52) U.S. Cl.
USPC ............ 424/439; 424/440; 424/441; 424/484

(58) Field of Classification Search
None
See application file for complete search history.

(56) References Cited

U.S. PATENT DOCUMENTS

| | | | |
|---|---|---|---|
| 4,197,289 A | 4/1980 | Sturzenegger et al. | 424/21 |
| 4,285,978 A | 8/1981 | Quinlivan | 426/87 |
| 4,548,825 A | 10/1985 | Voss et al. | |
| 4,771,295 A | 9/1988 | Baker et al. | 346/1.1 |
| 4,925,670 A | 5/1990 | Schmidt | 424/443 |
| 5,046,618 A * | 9/1991 | Wood | 206/532 |
| 5,070,410 A | 12/1991 | Hadley | 358/296 |
| 5,505,775 A | 4/1996 | Kitos | |
| 5,511,726 A | 4/1996 | Greenspan et al. | 239/102.2 |
| 5,543,164 A | 8/1996 | Krochta et al. | 426/302 |
| 5,609,908 A | 3/1997 | Voss | |
| 5,699,649 A | 12/1997 | Abrams et al. | 53/428 |
| 5,714,007 A | 2/1998 | Pletche et al. | 118/629 |
| 5,881,716 A | 3/1999 | Wirch et al. | |

(Continued)

FOREIGN PATENT DOCUMENTS

| | | |
|---|---|---|
| BE | 637 363 | 3/1964 |
| BE | 637363 A | 3/1964 |

(Continued)

OTHER PUBLICATIONS

Surgicel Product Sheet.

(Continued)

*Primary Examiner* — Isis Ghali

(57) ABSTRACT

A method of manufacturing a bioactive fluid dose on an ingestible sheet, comprising the steps of advancing the ingestible sheet to a dispense position, and activating a fluid ejector to dispense essentially a drop of a bioactive fluid onto the ingestible sheet.

16 Claims, 21 Drawing Sheets

U.S. PATENT DOCUMENTS

| | | | | |
|---|---|---|---|---|
| 5,894,841 | A | | 4/1999 | Voges ............... 128/203.12 |
| 5,925,732 | A | | 7/1999 | Ecker et al. |
| 5,960,609 | A | * | 10/1999 | Abrams et al. ............ 53/428 |
| 5,992,742 | A | * | 11/1999 | Sullivan et al. ...... 235/462.01 |
| 5,992,890 | A | | 11/1999 | Simcox ................. 283/66.1 |
| 6,007,630 | A | | 12/1999 | Pletcher et al. ........... 118/624 |
| 6,027,758 | A | | 2/2000 | McHugh et al. .......... 426/615 |
| 6,063,412 | A | | 5/2000 | Hoy ...................... 426/87 |
| 6,074,688 | A | | 6/2000 | Pletcher et al. ........ 427/2.14 |
| 6,086,942 | A | | 7/2000 | Carden et al. .............. 427/5 |
| 6,474,786 | B2 | * | 11/2002 | Percin et al. ............... 347/54 |
| 6,551,611 | B2 | * | 4/2003 | Elliesen et al. ........... 424/449 |
| 2002/0187248 | A1 | * | 12/2002 | Childers ................ 427/2.1 |

FOREIGN PATENT DOCUMENTS

| | | | |
|---|---|---|---|
| EP | 1096250 A2 | | 5/2001 |
| GB | 1 561 100 | | 2/1980 |
| GB | 1561100 A | | 2/1980 |
| GB | 2338896 A | * | 1/2000 |
| WO | WO 9501735 A1 | | 1/1995 |

OTHER PUBLICATIONS

GelFoam Product Sheet.

'Development of a High-Resolution Thermal Inkjet Printhead', by William A. Buskirk, David E. Hackleman, Stanley T. Hall, Paula H. Kanerek, Robert N. Low Kenneth E. Trueba, and Richard R. Van de Poll; from the "Hewlett-Packard Journal" Oct. 1998 pp. 107-113.

'Laser-Comparable Inkjet Text Printing', by Jamie H. Bohorques, Brian P. Canfield, Kenneth J. Courian, Frank Frogo, Corrina A.E. Hall, Clayton L. Holstun, Aneesa R. Scandalis, and Michele E. Shepard; from the "Hewlett-Packard Journal" Feb. 1994 pp. 263-271.

'The Third -Generation HP Thermal Inkjet Printhead', by J. Stephen Aden, Jaime H. Bohorquez, Douglas M. Collins, M. Douglas Crook, Andre Garcia and Ulrich E. Hess; from the "Hewlett-Packard Journal" Feb. 1994 pp. 295-299.

'Printhead Design' from "2000 Torrey Pines Reasearch" pp. 83-151.

Surgicel Product Sheet, 92/08/2001.

http://news.uns.purdue.edu/UNS/html4ever/020109.Basaran.inkjet. html; "Method improves inkjet nozzles for printing, manufacturing"; Purdue News, School of Chem. Eng., 5 pgs.

Alvin U. Chen; "A new method for significantly reducing drop radius . . . "; Physics of Fluids, vol. 14, No. 1, Jan. 2002, pp. L1-L4.

\* cited by examiner

LAMINATED INGESTIBLE DOSAGE FORM FOR DISPENSING MULTIPLE BIOACTIVE SUBSTANCES

CROSS-REFERENCE TO RELATED APPLICATION

This application is a continuation of U.S. application Ser. No. 10/028,450, filed Oct. 24, 2001, now U.S. Pat. No. 6,962,715, issued Nov. 8, 2005.

BACKGROUND

1. Field of the Invention

The present invention relates to a method and dosage form for manufacturing pharmaceutical doses. More particularly the present invention relates to a method for manufacturing pharmaceutical doses on an ingestible sheet.

2. Description of the Art

Oral administration of pharmaceuticals is one of the most widely used methods to provide effective therapy for a variety of illnesses. Many powdered medications are typically administered orally to a person in a dosage form such as tablets or capsules, while still others are in liquid form. The release of orally administered medications falls into two broad categories, buccal or sublingual administration, and oral dissolution. For example, enteric coated tablets that release the medication in the intestinal tract of the patient. Further, many individuals suffer from chronic health problems that require the regular administration of medicaments. Diseases such as diabetes, allergies, epilepsy, heart problems, AIDS, and even cancer requires the regular delivery of precise doses of medicaments if patients are to survive over long periods of time. Such chronic treatment creates the need to regularly obtain additional medication. This can be extremely troublesome for those patients that lack the mobility to easily travel to a pharmacist to refill medications, such as the elderly and infirm. Thus, a method and a dosage form that provides the ability to make custom doses, outside of the large pharmaceutical manufacturing plants, is desirable.

Most pharmaceuticals involve dosage units in the microgram to milligram range of the purified active ingredient or ingredients. Thus, many pharmaceutical doses in tablet or liquid form are made in formulations of a predetermined quantity of pharmaceutical units in each dose. Such pharmaceutical doses are frequently available in fixed different strengths, such as 50 mg, 100 mg, etc.

Unfortunately, such conventional oral dosage forms suffer from a number of disadvantages. Typically, to effectively handle and dispense small doses a considerable amount of adjuvant material must be added in order that the final dosage form is of a manageable size. Thus, typical methods for manufacturing include the mixing of the pure drug with various other substances commonly referred to as excipients or diluents that are therapeutically inert and acceptable by regulatory bodies, such as the FDA. Excipients may also protect the drug from deterioration by oxidation, humidity, and light. Palatability can be improved through the addition of flavorants and identification by use of colorants. This mixing process often requires the use of sophisticated, complex expensive machinery. Certain excipients may be needed to improve the flowability of the drug and diluents through the mixing machinery. Therefore, a method and dosage form that reduces the mixing of the active drug with other substances, and utilizes less complex and expensive machinery would also be desirable.

These therapeutically inactive or inert materials also have the disadvantage that each such material must be evaluated before use in terms of potential incompatibilities with the medicaments present. For example, some of these materials, such as lubricants or disintegrants, may present problems concerning the bioavailability of the active ingredient. Further, the certification of new drugs is a lengthy and costly process involving animal studies followed by chemical trials to establish both the efficacy and safety of the new drug. Because a pharmaceutical's characteristics may be affected by changes in manufacturing and/or packaging, the approval process limits the approval to a particular manufacturing and packaging process. Thus, the ability to rapidly and easily change dosage units is extremely limited in conventional pharmaceutical manufacturing processes.

Drugs with a narrow therapeutic range must also be precisely dosed. If the patient falls below the range, the desired effect will not occur. However, if the patient is above the range then the risk of toxic effects increases. Clinicians assume the dose units manufactured are uniform and that generic equivalents have equal bioavailability. The many FDA generic formulation rejections and recalls for pharmaceuticals that have too high or low of a drug level, however, are evidence that accuracy and precision are still challenges for pharmaceutical manufacturing.

The ability to easily make a custom dose using tablets or capsules utilizing current technology is also difficult. It is virtually impossible to split or divide a capsule to decrease the dose administered requiring that the smallest dose be predetermined. Further, in the case of tablets a patient or pharmacist may often encounter difficulty in splitting or dividing even relatively large tablets that have a notch or groove at a predetermined breaking point to form a lower dosage unit. The splitting or breaking often results in fragments of unequal size. Thus, a method and dosage form that allows for variable doses to be formed outside the pharmaceutical manufacturing plant is desirable.

SUMMARY OF THE INVENTION

A method of manufacturing a bioactive fluid dose on an ingestible sheet, comprising the steps of advancing the ingestible sheet to a dispense position, and activating a fluid ejector to dispense at least one drop of a bioactive fluid onto the ingestible sheet.

BRIEF DESCRIPTION OF THE DRAWINGS

FIG. 5b is a cross-sectional view of the ingestible sheet shown in FIG. 5a.

FIG. 10b is a cross-sectional view of a dosage form manufactured using the process shown in FIG. 10a;

DESCRIPTION OF THE PREFERRED EMBODIMENTS

The present invention advantageously uses the multi-drop deposition capability of a fluid ejection cartridge to dispense pharmaceuticals on an ingestible sheet. Although one embodiment describes the use of a thermally activated fluid ejection cartridge to dispense medications in the form of drops on an ingestible media, other methods of activation such as, piezoelectric and acoustic activation may also be used in the present invention. The fluid ejection cartridge of the present invention is a drop-on-demand type fluid dispenser. The present invention provides greater control of the drug dose than a typical diluting and mixing apparatus by producing precise and repeatable doses onto an ingestible sheet. Another feature of the present invention is the ability to dispense multiple different pharmaceuticals in varied quantities onto an ingestible sheet.

For purposes of this description and the present invention, the term "bioactive" as used with fluid, composition, substance, or agent, is a composition that affects a biological function of a vertebrate directly or as a result of a metabolic or chemical modification associated with the vertebrate or its vicinal environment. An example of a bioactive fluid is a pharmaceutical substance, such as a drug, which is given to alter a physiological condition of the vertebrate, such as a disease. A bioactive fluid is meant to include any type of drug, medication, medicament, vitamin, nutritional supplement, or other compound that is designed to affect a biological function of a vertebrate.

Figure 1A:
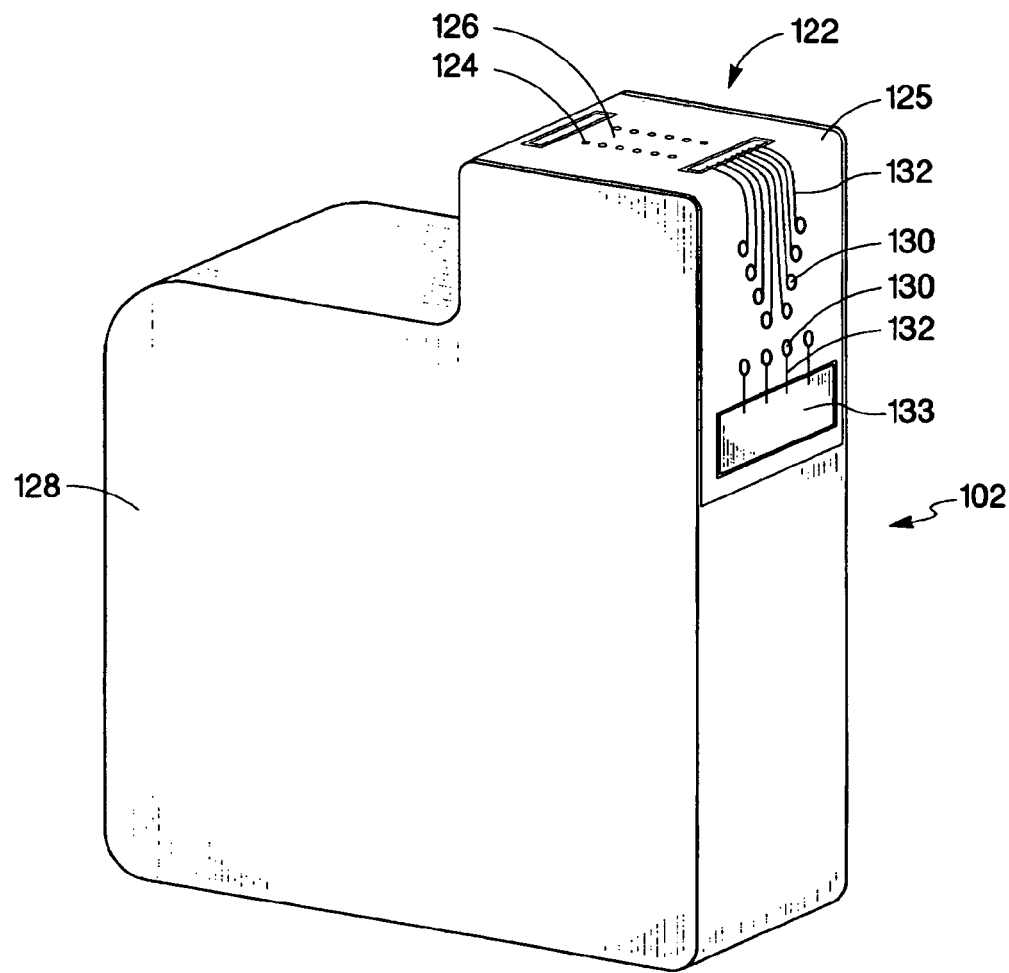
FIG. 1a is a perspective view of a bioactive fluid cartridge according to an embodiment of this invention.

Referring to FIG. 1a, an exemplary embodiment of a fluid ejection cartridge 102 of the present invention is shown in a perspective view. In this embodiment, a fluid reservoir 128, in the body portion of the fluid ejection cartridge 102, typically contains either a bioactive fluid used to generate the pharmaceutical dose or an ingestible ink used to generate an image or characters on an ingestible sheet or other material used to make a dosage form. The fluid reservoir 128 is fluidically coupled, preferably through internal passageways, to a substrate (not shown) that is attached to the back of a nozzle layer 126. The substrate (not shown) normally contains an energy-generating element or fluid ejector (not shown) that generates the force necessary for ejecting the fluid held in the reservoir. Two widely used energy generating elements are thermal resistors and piezoelectric elements. The former rapidly heats a component in the fluid above its boiling point causing vaporization of the fluid component resulting in ejection of a drop of the fluid. While the latter utilizes a voltage pulse to generate a compressive force on the fluid resulting in ejection of a drop of the fluid. For more information on various transducers utilized in drop-on-demand fluid ejection cartridges see Stephen F. Pond, Ph.D. *Inkjet Technology and Product Development Strategies*, ch 4 (Torrey Pines Research, 2000); and more particularly for thermal inkjet technology see J. Stephen Aden et al., *The Third-Generation HP Thermal Ink-Jet Printhead*, Hewlett-Packard Journal, vol. 45, no. 1, pg. 41-45, February 1994.

The substrate (not shown), the nozzle layer 126, nozzles 124, and a flexible circuit 125 form what is generally referred to as an ejector head 122. In other embodiments the ejector head 122 includes the substrate (not shown), the nozzle layer 126 and the nozzles 124. The nozzle layer 126 contains one or more nozzles 124 through which fluid, that is contained in a chamber around the fluid ejectors, is ejected by activation of the fluid ejectors (not shown) located in close proximity to the nozzles 124. Each activation of a fluid ejector results in the ejection of a precise quantity of fluid in the form of a fluid drop; thus, the number of activations of the fluid ejector controls the number of drops ejected. For more information on drop formation see for example Jaime H. Bohorquez et al., *Laser-Comparable Inkjet Text Printing*, Hewlett-Packard Journal, vol. 45, no. 1, pg. 9-17, February 1994; or William A.

Buskirk et al., *Development of a High Resolution Thermal Inkjet Printhead*, Hewlett-Packard Journal, vol. 39, no. 5, pg. 55-61, October 1988.

The fluid ejection cartridge 102 described in the present invention can reproducibly and reliably eject drops in the range of from about ten femto-liters to about ten micro-liters depending on the parameters of the fluid ejection cartridge such as the size and geometry of the chamber around the fluid ejector, the size and geometry of the fluid ejector, and the size and geometry of the nozzle. Thus, the present invention has the ability to accurately dispense a bioactive fluid with a part per million to a part per billion accuracy. This is particularly advantageous when dispensing expensive bioactive substances, such as certain hormones, antibiotics, and bioactive fluids derived from some natural products in scarce supply. The accuracy and precision is advantageous when dispensing concentrated substances with high potency. In addition, a further advantage of utilizing the fluid ejection cartridge 102 of the present invention is a reduction, to less than one percent by weight, in the amount of excess bioactive fluid that is dispensed to assure proper label dosage. This embodiment is also advantageous for utilizing a mixture of the bioactive fluid and an ingestible ink contained in the fluid reservoir 128.

The nozzle layer 126 may be formed of metal, polymer, glass, or other suitable material such as ceramic. Preferably, the nozzle layer 126 is formed from a polymer such as polyimide, polyester, polyethylene naphthalate (PEN), epoxy, or polycarbonate. In an alternate embodiment, the nozzle layer 126 is formed from a metal such as a nickel base enclosed by a thin gold, palladium, tantalum, or rhodium layer. Preferably, the components of the ejector head 122 and the fluid reservoir are formed of materials that are inert to the bioactive fluid and/or the ingestible ink which are to be dispensed therefrom. Thus, inert materials such as glass, ceramic, stainless steel, noble metals, and polymers inert to the bioactive fluid are preferred.

The fluid is selectively expelled from the one or more of the nozzles 124 by electrical signals communicated through electrical contacts 130 and associated conductive traces 132 disposed on the flexible circuit 125. In the preferred embodiment, the flexible circuit 125 is typically bent around an edge of the fluid ejection cartridge 102 and secured. The electrical traces 132 are routed from the electrical contacts 130 to bond pads on the substrate (not shown) to provide electrical connection for the fluid ejection cartridge 102. Thus, by communicating the proper electrical signal through the electrical contacts 130 a fluid ejector is activated the appropriate number of times to eject a predetermined number of drops.

An information storage element 133 is disposed on cartridge 102. Preferably, the information storage element 133 is coupled to a flexible circuit such as the flexible circuit 125 as shown in FIG. 1a. The information storage element 133 is any type of memory device suitable for storing and outputting information that may be related to properties or parameters of the bioactive fluid contained within the fluid reservoir 128. Preferably, the information storage element 133 is a memory chip mounted on the flexible circuit 125 and electrically coupled through the electrical traces 132 to the electrical contacts 130. Alternatively, the information storage element 133 can be encapsulated in its own package with corresponding separate electrical traces and contacts.

When the fluid ejection cartridge 102 is either inserted into, or utilized in, a dispensing system the information storage element 133 is electrically coupled to a controller that communicates with the information storage element 133 to use the information or parameters stored therein. However, other forms of information storage can also be utilized for the information storage element 133, such as a bar code or other device that allows storage of information. Further, the information storage element 133 can be mounted elsewhere on or within the body of the fluid ejection cartridge 102 with appropriate contacts and electrical connections to access the storage element depending on the particular application. In addition, the information storage element 133 can also be placed on an off-axis container utilized with semi-permanent ejector heads or cartridges.

The information storage element 133 may contain information such as the particular bioactive fluid or other material contained in the fluid reservoir 128; the quantity of material remaining in the fluid reservoir 128 based on the number of drops dispensed or the number of times the fluid ejector has been activated. Other information can include the date of manufacture, inspection dates, quality control information, dispensing system parameters, and customer/patient information.

Figure 1B:
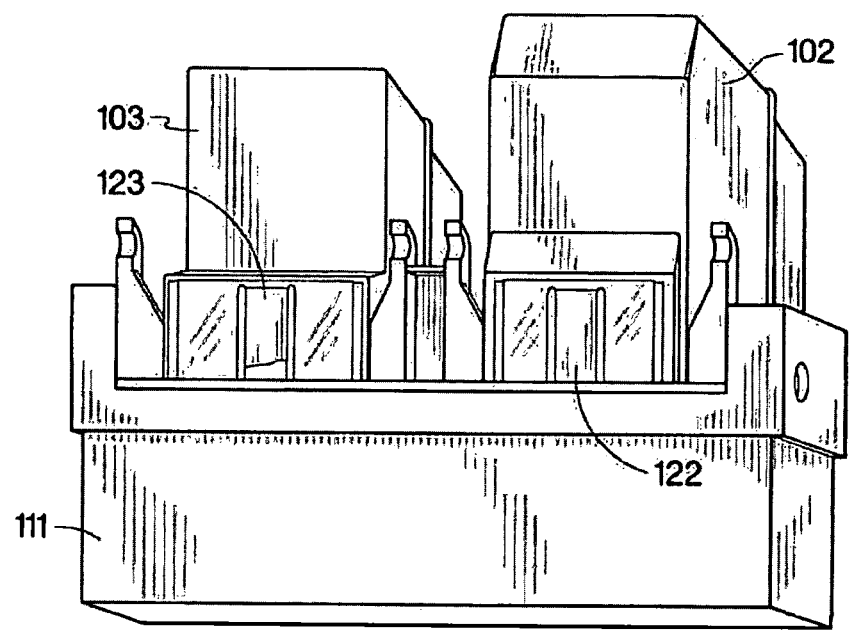
FIG. 1b is a perspective view of fluid ejection cartridges held within a carriage according to an embodiment of this invention.

The fluid ejection cartridge 102, or more preferably a set of individual fluid ejection cartridges 102 and 103, capable of ejecting drops of bioactive fluid or ingestible ink or a combination thereof from ejector heads 122 and 123 are held within a carriage 111, as illustrated in a perspective view in FIG. 1b. Alternative embodiments can include one or more semi-permanent ejector heads that are replenished from one or more fluidically-coupled off-axis fluid containers, or a single fluid ejection cartridge having one or more fluids available within the fluid ejection cartridge and fluid ejecting nozzles designated for each fluid integrally coupled with each fluid reservoir, or a single fluid ejection cartridge having a mixture of the bioactive fluid and ingestible ink. The present invention can be satisfactorily employed by at least these alternatives.

Figure 1C:
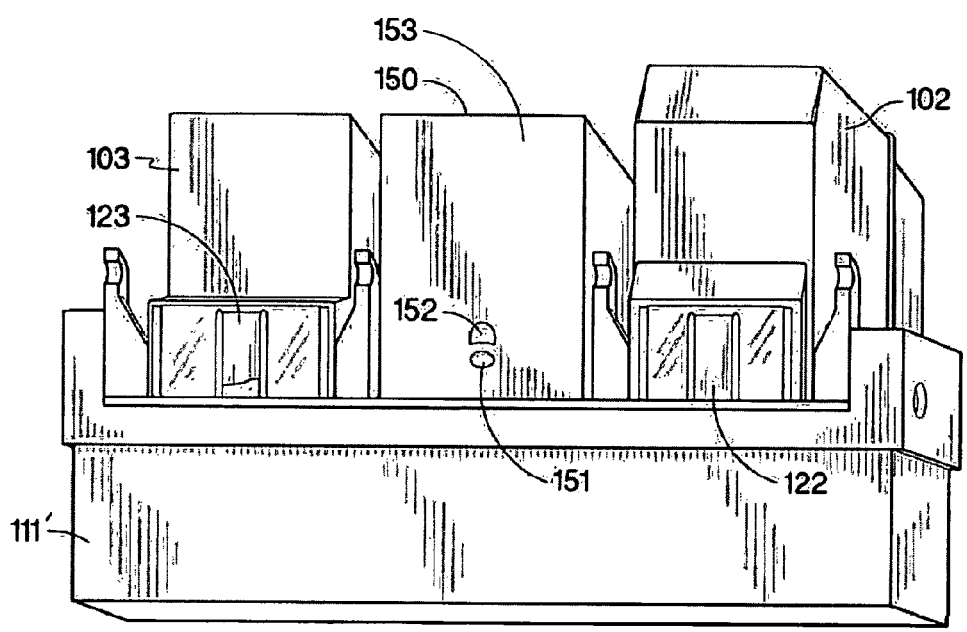
FIG. 1c is a perspective view of fluid ejection cartridges and an image acquisition system held within a carriage according to an alternate embodiment of this invention.

An alternate embodiment of the present invention where a carriage 111' contains an image acquisition system 150 is shown in FIG. 1c. In this embodiment, the image acquisition system 150 contains a camera 151 and a light source 152. As the cartridge 102 ejects drops of a bioactive fluid onto the ingestible sheet, the drops may exhibit spots on the sheet having various visual or otherwise detectable geometric aspects, such as area extent, shape, and position. Preferably, the light source 152 is positioned relative to the camera 151 so that the camera 151 can image these detectable geometric aspects. Although as depicted in FIG. 1c the light source 152 comprises a single source, multiple sources can also be used. The light source 152 is preferably a light emitting diode (LED), although other light sources such as light bulbs or lasers can also be utilized.

Figure 2A:
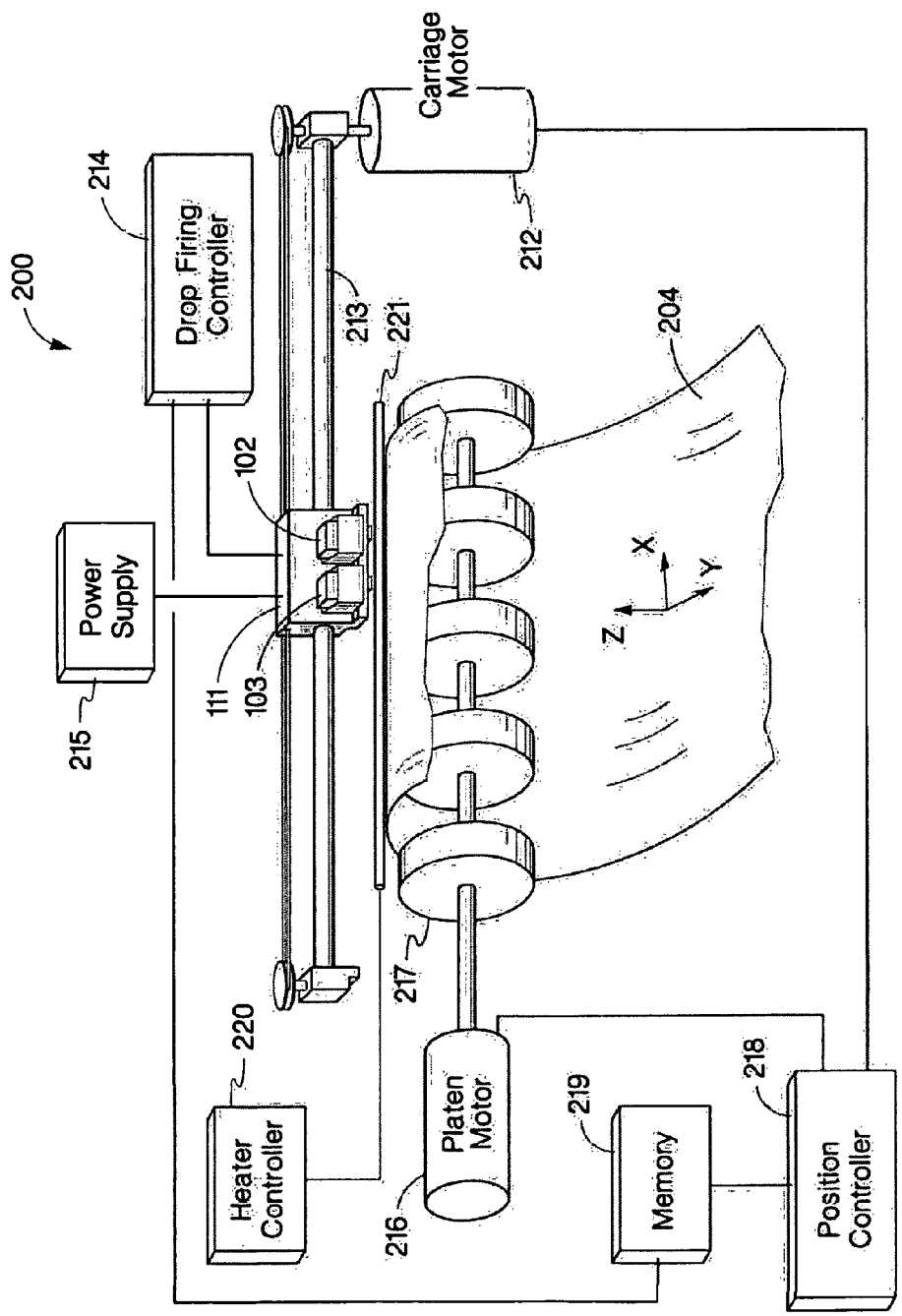
FIG. 2a is a perspective view of a bioactive fluid dispensing system according to an embodiment of this invention.

The image acquisition system 150 also contains, a camera and light source, controller 153 that is preferably coupled to a drop-firing controller 214 as shown in FIG. 2a. When either fluid ejection cartridge 102 or 103 is activated by the drop-firing controller 214, to dispense bioactive fluid or ingestible ink on an ingestible sheet, the camera controller 153 is correspondingly triggered by the drop-firing controller 214; thus activating the camera 151 to gather image information pertaining to a portion of the surface of an ingestible sheet on which either a bioactive fluid or ingestible ink has been deposited. The camera 151 as shown in FIG. 1c can be any camera that can image the desired qualities on an ingestible sheet such as a camera that captures 2 dimensional images or line scan cameras that capture a narrow-stripped portion of the surface being imaged and these narrow-stripped portions are combined to for a complete two dimensional image.

In addition to capturing images of either the bioactive fluid or ingestible ink or other material dispensed on the ingestible sheet the image acquisition system 150 can also be utilized to capture images of information that has been placed on an ingestible sheet prior to deposition of the bioactive fluid or ingestible ink. Examples of such information are the composition of the ingestible sheet or results of quality control testing; data on compatibility with the bioactive fluids, i.e. whether the ingestible sheet is compatible or incompatible with bioactive fluid being dispensed; patient information such as height, weight, name, age, prescribed dose etc.; expiration dates, temperature and/or humidity sensors, indicating that the ingestible sheet is no longer effective or it has been exposed to an extreme which could hinder its effectiveness. Although the image acquisition system 150, as depicted in FIG. 1*c*, is mounted in carriage 111', other arrangements can also be utilized such as mounting the image acquisition system 150 on a separate carriage, or locating the image acquisition system in a different portion of a bioactive fluid dispensing system 200 shown in FIG. 2*a*.

The essential parts of a bioactive fluid dispensing system 200 according to an embodiment of the present invention is shown in a block diagram in FIG. 2*a*. In this embodiment, a platen to which an ingestible sheet 204, such as a starch or glycerin based paper, is transported by mechanisms that are known in the art. The carriage 111 is typically supported by a slide bar 213 or similar mechanism within the system 200 and physically propelled along the slide bar 213 to allow the carriage 111 to be translationally reciprocated or scanned back and forth across the ingestible sheet 204. The scan axis, X, is indicated by an arrow in FIG. 2*a*.

Under control of the drop firing controller 214 and a position controller 218, the carriage 111 scans across the ingestible sheet 204, and fluid drops are selectively ejected from fluid ejectors disposed within the fluid ejection heads of the set of fluid ejection cartridges 102 and 103 onto the ingestible sheet 204. The power to activate the fluid ejectors is supplied by a power supply 215. The drops are ejected to form predetermined dot matrix patterns, forming both the pharmaceutical dose from the cartridge containing the bioactive fluid, and images or alphanumeric characters from the cartridge containing the ingestible ink.

Rasterization of the data can occur in a host computer such as a personal computer or PC (not shown) prior to the rasterized data being sent, along with the system control commands, to the system, although other system configurations or system architectures for the rasterization of data are possible. This operation is under control of system driver software resident in the system's computer. The system interprets the commands and rasterized data to determine which drop ejectors to fire. An arrow in FIG. 2*a* indicates the fluid drop trajectory axis, Z, directed from the fluid ejection cartridges 102 and 103 toward the ingestible sheet 204. When a swath of fluid ejection has been completed, the ingestible sheet 204 is moved an appropriate distance along the ingestible sheet axis, Y, indicated by the arrow, in preparation for the next swath. This invention is also applicable to bioactive fluid dispensing systems employing alternative means of imparting relative motion between the fluid ejection cartridges and the ingestible sheet, such as those that have fixed fluid ejection cartridges and move the ingestible sheet in one or more directions, and those that have fixed ingestible sheet and move the fluid ejection cartridges in one or more directions.

As can be appreciated from a preferred embodiment shown in FIG. 2*a*, the ingestible sheet 204 is advanced into a fluid ejection area beneath the ejector heads 122 and 123 (shown in FIG. 1*b*) by a sheet positioning mechanism commonly referred to as a sheet positioner or sheet advancer including rollers 217, a platen motor 216, and traction devices (not shown). In a preferred embodiment, the fluid ejection cartridges 102 and 103 are incrementally drawn across the ingestible sheet 204 on the platen by a carriage motor 212 in the ±X direction, perpendicular to the Y direction of entry of the medium. The platen motor 216 and the carriage motor 212 are typically under the control of the sheet and cartridge position controller 218. An example of such a positioning and control apparatus may be found described in U.S. Pat. No. 5,070,410. Thus, the ingestible sheet 204 is positioned in a location so that the fluid ejection cartridges 102 and 103 may eject drops of fluid onto the ingestible sheet 104 as required for the particular dose being generated, and the particular data being written that is input to the drop-firing controller 214 of the bioactive fluid dispensing system 200. These drops of fluid are expelled from selected orifices in the ejector heads 122, 123 (as shown in FIG. 1*b*) in a band parallel to the scan direction as the fluid ejection cartridges 102 and 103 are translated across the ingestible sheet 204 by the carriage motor 212. Once the fluid ejection cartridges 102 and 103 have reached the end of their traverse in the X direction on the slide bar, they are either returned back along the support mechanism while continuing to eject fluid or returned without fluid ejection.

When the fluid ejection cartridges 102, 103 reach the end of their travel at an end of a fluid ejection swath on the ingestible sheet 204, the ingestible sheet 204 is conventionally incrementally advanced by the position controller 218 and the platen motor 216. Once the fluid ejection cartridges have reached the end of their traverse in the X direction on the slide bar 213 or similar support mechanism, they are either returned back along the slide bar 213 while continuing to eject fluid or returned without ejecting. The ingestible sheet 204 may be advanced by an incremental amount equivalent to the width of the fluid-ejecting portion of the fluid-ejecting head or some fraction thereof related to the spacing between the nozzles. Control of the ingestible sheet 204, positioning of the fluid ejection cartridge, and selection of the correct fluid ejectors for creation of both the bioactive fluid dose and the image or character written is determined by the position controller 218 and the drop-firing controller 214. The controllers may be implemented in a conventional electronic hardware configuration and provided operating instructions from conventional memory 219.

The bioactive fluid dispensing system 200 also contains a heater 221 coupled to a heater controller 220 as shown in FIG. 2*a*. The heater 221 heats the ingestible sheet 204 to remove water and other solvents deposited on the ingestible sheet 204 after deposition of the bioactive fluid or ingestible ink. The heater also contains a temperature sensor (not shown) that is coupled to the heater controller 220 to maintain the ingestible sheet 204 at the appropriate temperature. The particular temperature that the temperature sensor maintains depends on the particular bioactive fluid or ingestible ink being dispensed, and on the particular ingestible sheet 204 being utilized. Although the heater 221 is located above the rollers 217 as depicted in FIG. 2*a* the heater can also be located in other portions of the bioactive fluid dispensing system 200 such as underneath the ingestible sheet 204 in front of the rollers 217.

Figure 2B:
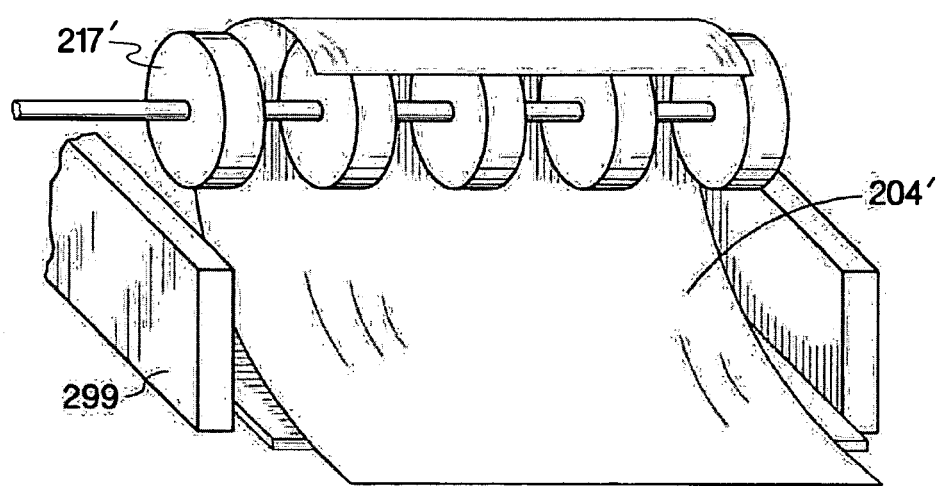
FIG. 2b is a perspective view of a bioactive fluid dispensing system with an ingestible sheet tray according to an alternate embodiment of this invention.

A perspective view of an alternate embodiment of the present invention where the bioactive fluid dispensing system 200 includes an ingestible sheet tray 299 is shown in FIG. 2*b*. In this embodiment, the tray 299 holds separate ingestible sheets 204' that are advanced into the fluid ejection area beneath ejector heads (not shown) by rollers 217' and other mechanisms as described above in FIG. 2*a*. Preferably the tray 299 holds from 1 to about 250 sheets, however, depending on the particular system, ingestible sheet, and bioactive fluid being utilized, the tray 299 may hold more than 250 sheets.

The apparatus described above makes unique use of an automated fluid ejecting device, having at least one bioactive fluid supply in a reservoir or chamber and at least one, and preferably, a plurality of fluid ejectors in an array, each ejector dispensing a precise volume of fluid in essentially individual droplets on each activation of the fluid ejector. This arrangement enables the quantity of the bioactive fluid dispensed to be varied in a specified area of the ingestible sheet thereby enabling either custom, or a wide range of doses to be more easily prepared. The apparatus or system as depicted in FIGS. 2a and 2b may be used in a manufacturing environment, a pharmacy, or even in other dispensing locations such as in a hospital, home etc. to automatically prepare pharmaceutical doses in response to patients needs.

Figure 3:
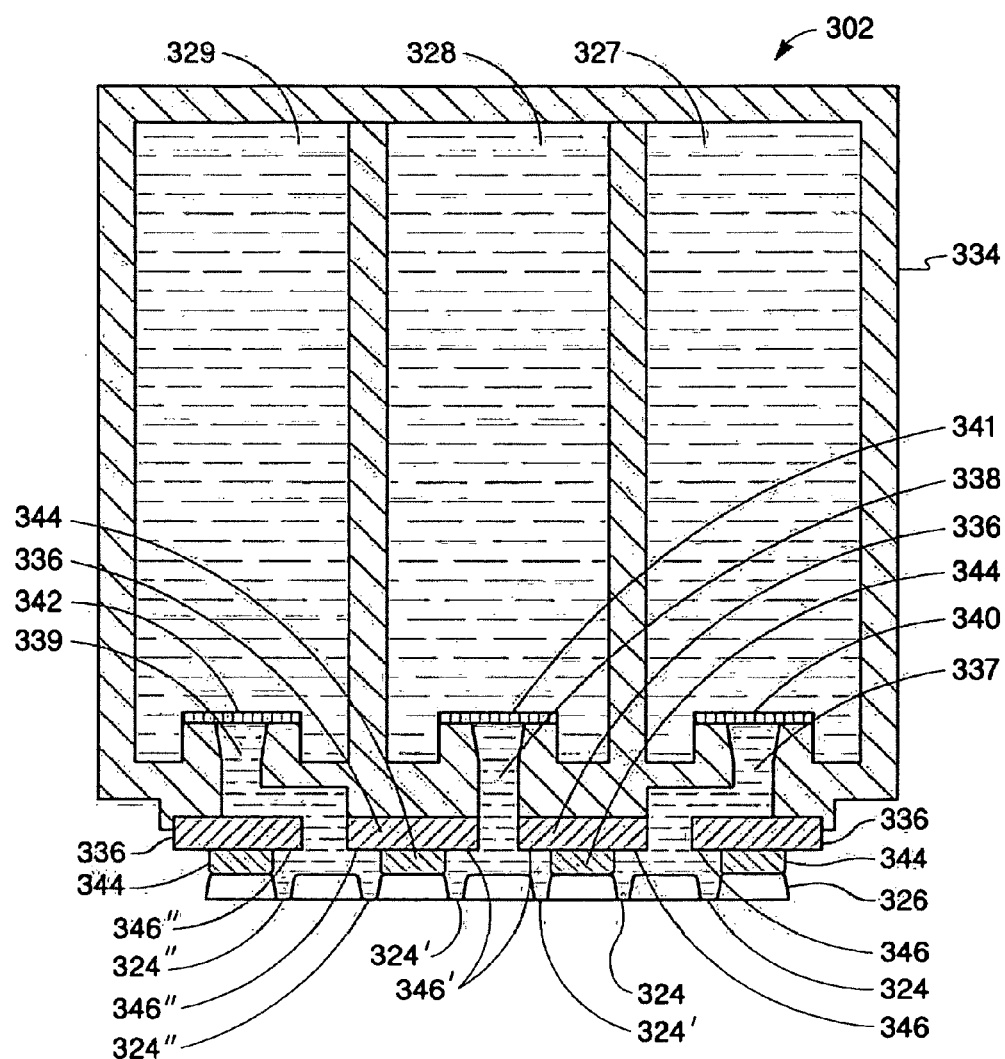
FIG. 3 is a cross-sectional view of a fluid ejection cartridge according to an alternate embodiment of this invention.

A cross-sectional view of an alternate embodiment of the present invention where a fluid ejection cartridge 302 includes three fluid reservoirs 327, 328, and 329 contained within a cartridge body 334 is shown in FIG. 3. In this embodiment, a substrate 336 is attached to the outer surface of the cartridge body 334, and includes three groups of fluid ejectors 346, 346' and 346", in fluid communication with the three fluid reservoirs 327, 328, and 329 via three fluid routing channels 337, 338, and 339 respectively. Three fluid filters 340, 341, and 342, are mounted within the fluid reservoirs 327, 328, and 329, respectively. These filters are preferably constructed from stainless steel wire mesh of a desired porosity to provide good filtration of solid particles and air bubbles when fluid passes from the three fluid reservoirs 327, 328, and 329 into the three fluid routing channels 337, 338, and 339.

Attached to the substrate 336 is a firing chamber layer 344 that defines the volume around each fluid ejector. Attached to the firing chamber layer 344 is a nozzle layer 326 that contains three groups of nozzles 324, 324' and 324". The fluid will flow from the three fluid reservoirs 327, 328, and 329 through the three fluid filters 340, 341, and 342 into the three fluid output ports 337, 338, and 339 through the substrate 336. A firing chamber layer 344 includes fluid channels (not shown) and a firing chamber (not shown) formed into the layer that feeds fluid to the ejectors 346, 346' and 346". Upon appropriate activation, the ejectors 346, 346' and 346" initiate the ejection of fluid out of the fluid ejection cartridge 302 through the three groups of nozzles 324, 324' and 324". Preferably, each group of nozzles is in a column and more preferably in staggered columns, however other patterns, such as circular patterns can also be utilized. This embodiment is particularly advantageous when the user desires a self-contained cartridge or integral replaceable unit containing the bioactive fluid, the ingestible ink, and a protective coating that is dispensed over the dispensed bioactive fluid. This embodiment is also advantageous when the user has three compatible bioactive fluids that can be dispensed on the same sheet.

Although the properties of the ingestible sheets used in accordance with the present invention depend both on the particular bioactive fluid being dispensed and on the particular materials utilized in the sheet, it is generally preferable that the sheets are safely edible or ingestible, and do not have an objectionable "feel" in the mouth. In addition, the sheets preferably dissolve or degrade in body fluids and/or enzymes. However, the sheets can be made of non-degradable materials that are readily eliminated by the body. Preferably the sheets are hydrophilic and readily disintegrate in water and more preferably the dissolution or disintegration of the sheets is enhanced at the pH of the fluids in the stomach or upper intestine. Further, ingestible sheets that minimize unintended interactions with the bioactive fluid dispensed on the sheets and sheets that minimize the release of any sheet component that would cause unintended interactions with the bioactive fluid upon dissolution of the sheet, are also desirable.

Additional properties of the ingestible sheet that are desirable are the ability to remain stable over extended periods of time, at elevated temperatures, and at high or low levels of relative humidity. In addition, it is also preferable that the ingestible sheets are generally a poor medium for the growth of microorganisms to reduce spoilage. Further, ingestible sheets that possess reasonable mechanical properties such as tensile strength and tear strength are desirable to allow the sheets to be processed through the various steps of fabrication of the final dosage form using methods such as are recognized in the art.

Ingestible sheets that can be utilized in the present invention can be one or a mixture of organic film formers generally classified into two broad categories, i.e. polymeric and paper. Examples of such film formers are starch (i.e. both natural and chemically modified) and glycerin based sheets with or without a releasable backing. Other examples include, proteins such as gelatin, cellulose derivatives such as hydroxypropylmethylcellulose and the like; other polysaccharides such as pectin, xanthan gum, guar gum, algin and the like; synthetic polymers such as polyvinyl alcohol, polyvinylpyrrolidone and the like. Examples of ingestible sheets or edible films that can be utilized are those that are based on milk proteins, rice paper, potato wafer sheets, and films made from restructured fruits and vegetables.

In particular, sheets or films made from restructured fruits and vegetables are advantageous were it is desirable to mask or modify the taste or smell of the bioactive fluid being delivered. Further, these restructured fruit and vegetable films also provide a convenient approach to encourage children to take various medications as well as providing a more pleasing and varied taste for various medications taken by adults. For more information on restructured fruit and vegetable films, see for example U.S. Pat. No. 5,543,164 and U.S. Pat. No. 6,027,758.

Dispensing the bioactive fluid on an ingestible sheet containing a water-expandable foam is preferable for those applications desiring rapid release of the bioactive fluid once ingested. Examples of such materials are an oxidized regenerated cellulose commercially available from Johnson and Johnson under the trademark SURGICEL®, and a porcine derived gelatin powder commercially available from Pharmacia Corporation under the trademark GELFOAM®.

The form of the ingestible sheet that can be utilized in the present invention can be any of the forms generally recognized in the art such as those used for paper, cardboard or polymeric films. The ingestible sheet or roll preferably is uniform in thickness and in width. Although the thickness of the ingestible sheet will depend on the particular bioactive fluid being dispensed, the particular ingestible sheet being utilized, and the particular method of manufacture used; the thickness of the ingestible sheet preferably ranges from about 10 to about 350 microns and more preferably from about 25 to about 100 microns thick.

The dosage forms produced in accordance with the present invention are eminently suited to span the range of production from individualized doses made in a home or hospital environment to the high speed high volume production in a pharmaceutical manufacturing environment. Thus, the particular width and length will not only depend on both the particular bioactive fluid being dispensed and the particular ingestible sheet being utilized, but more particularly on the particular method of manufacture used. Thus, the ingestible sheet can be in roll or individual sheet forms with widths varying from approximately one centimeter to several meters, and lengths from a few centimeters to several thousand meters, although other lengths and widths can also be utilized.

Figure 4:
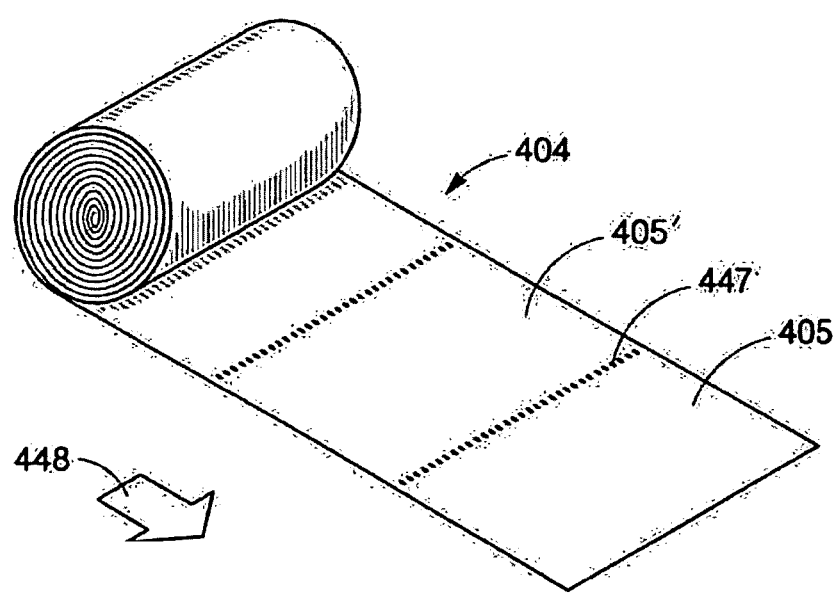
FIG. 4 a perspective view of an ingestible sheet according to an embodiment of this invention.

An embodiment of an ingestible sheet that is preferable for both high speed high volume manufacturing as well as for custom, individualized dispensing is illustrated in a perspective view in FIG. 4. In this embodiment, an ingestible sheet 404 is in the form of a roll that contains perforations 447 that delineates each dosage form 405 and 405'. In this embodiment, a bioactive fluid is dispensed preferably in a two-dimensional array, although other patterns can also be utilized, onto a first portion of the ingestible sheet 404. A sheet advancer (not shown) then advances the ingestible sheet 404 and a second two dimensional array or alternate pattern is dispensed on a second portion of the ingestible sheet. The first and second portions form dosage forms 405 and 405' respectively.

Preferably, after the bioactive fluid is dispensed on the dosage form 405 the user or system separates the dosage form 405 from the dosage form 405' by tearing, by cutting along the perforations 447, or by punching out the dispensed areas of the sheet. The user or system can also separate the dosage form 405 from the dosage form 405' before dispensing of the bioactive fluid. This embodiment is particularly advantageous for systems such as those that have fixed fluid ejection cartridges; however, it can also be utilized in other systems as well. Preferably, the ejector head is approximately the width of the ingestible sheet 404 and the platen (not shown) moves the ingestible sheet in the direction of arrow 448 allowing both the dispensed dose of bioactive fluid as well as the appropriate characters or symbols utilizing the ingestible ink to be formed.

Figure 5A:
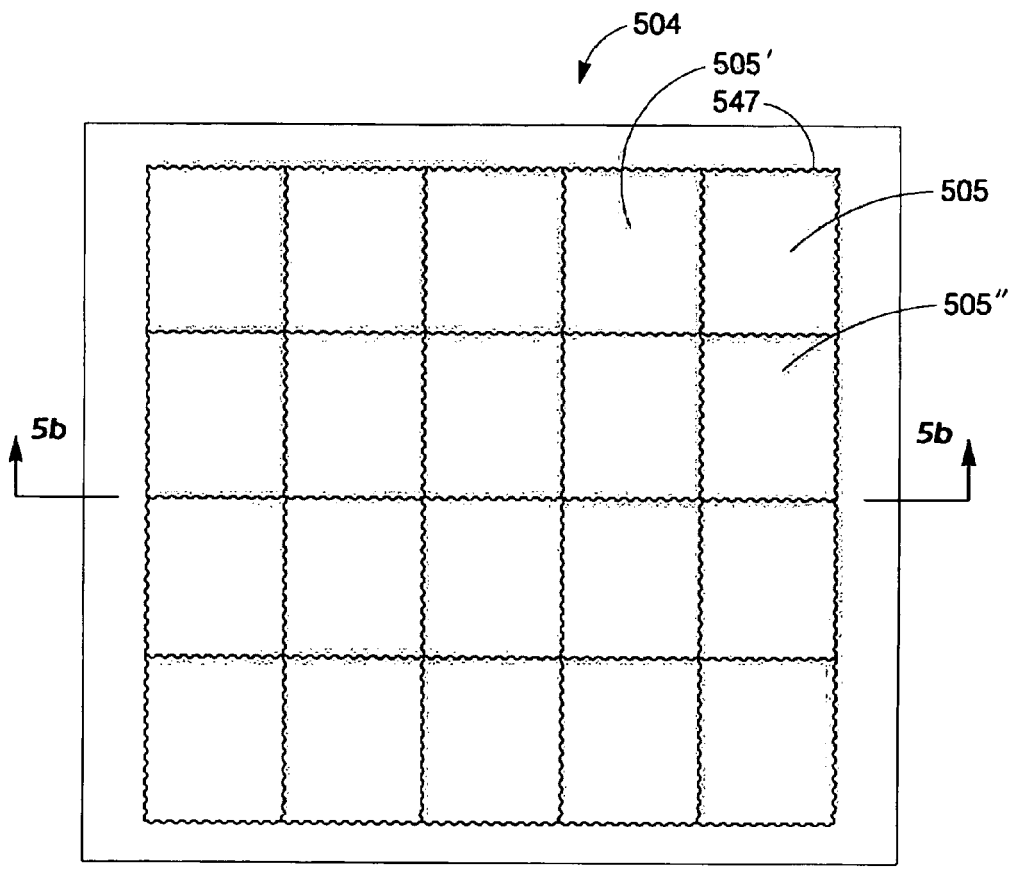
FIG. 5a is a plan view of an ingestible sheet according to an alternate embodiment of this invention.
Figure 5B:
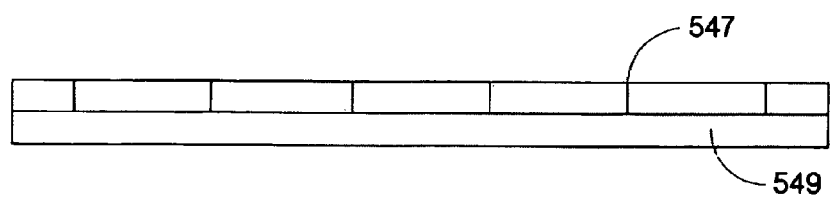

An alternate embodiment of an ingestible sheet that can also be used for custom, individualized pharmaceutical doses is shown in a plan view in FIG. 5a and in a cross-sectional view in FIG. 5b. In this embodiment, an ingestible sheet 504 is in the form of a sheet with a plurality of dosage forms 505 where each dosage form 505 contains dosage form separators 547 around its peripheral edge. Preferably, after the bioactive fluid is dispensed on the plurality of the dosage forms 505 contained in the ingestible sheet 504 the user or system separates the dosage form 505 from the dosage forms 505' and 505" by bending or, by pushing up in the center of the dosage form 505, or some other convenient method and peeling the dosage form 505 from a releasable backing 549 shown in FIG. 5b. This embodiment is particularly advantageous for systems used to dispense custom pharmaceutical doses at home, in a hospital or a pharmacy; however, it can also be utilized in other systems as well. Although FIG. 5a shows the ingestible sheet 504 utilizing dosage form separators 547, the ingestible sheet 504 can utilize any convenient means of separation such as perforations shown in FIG. 4.

Figure 6A:
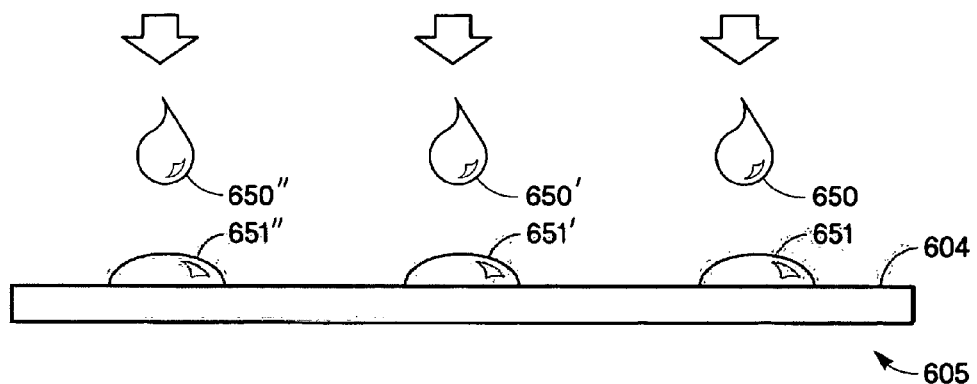
FIG. 6a is a cross-sectional view of a method for generating a dosage according to an embodiment of this invention.

An embodiment of a method for generating a dosage form where the bioactive fluid is dispensed onto the ingestible sheet is shown in a cross-sectional view in FIG. 6a. In this embodiment, a drop-firing controller in a fluid dispensing system (not shown) activates one and, typically, a plurality of fluid ejectors, of a fluid ejection cartridge (not shown), to eject fluid drops 650, 650', and 650" of the bioactive fluid onto an ingestible sheet 604 forming deposits 651, 651', and 651", respectively. For clarity in understanding the invention, the fluid drops 650, 650', and 650" are shown as being deposited on the surface of the ingestible sheet 604. Although this will occur for non-porous, non-absorbing ingestible sheets, typically, the ingestible sheet 604 will be a porous and absorbing material which will allow the bioactive fluid to be absorbed into the interior of the ingestible sheet 604. A dosage form 605 is generated when the required number of fluid drops of the bioactive fluid, to create the desired pharmaceutical dose, have been dispensed on a portion of the ingestible sheet 604. Preferably, the dosage form 605 contains a two-dimensional array of the deposits 651, 651' and 651" of the bioactive fluid on the ingestible sheet 604. However, other arrangements can also be utilized, such as overlapping deposits forming a layer, or a different geometrical arrangement of the deposits 651, 651', and 651".

Figure 6B:
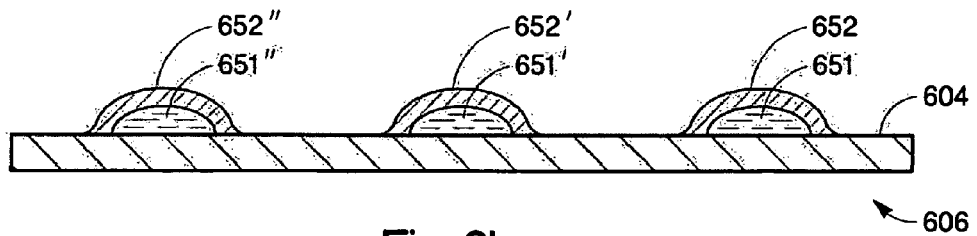
FIG. 6b is a cross-sectional view of a method for generating a dosage according to an alternate embodiment of this invention.

An alternate embodiment of the present invention where the process used for generating a dosage form includes a barrier material deposited over the bioactive fluid is shown in a cross-sectional view in FIG. 6b. In this embodiment, the drop-firing controller activates one and, typically, a plurality of fluid or barrier ejectors, to eject fluid drops of a barrier material over the deposits 651, 651', and 651" of the bioactive fluid to form barrier deposits 652, 652", and 652". The barrier deposits 652, 652', and 652" and deposits 651, 651', and 651" of the bioactive fluid on the ingestible sheet 604 form dosage form 606. The barrier material acts to seal the bioactive fluid from the environment. Depending on the particular bioactive fluid dispensed, and the particular ingestible sheet used, the barrier material provides various protective properties, such as humidity protection, protection from oxidation, inactivation, or contamination. The barrier material is an edible coating made from a suitable polymeric material such as a water-soluble polyoxyethylene or cellulose ether derivative. In addition, preferably the barrier material is an inert material, which will not interact with the deposited bioactive fluid. Further, the barrier material may also act as an adhesive as will be discussed later. In this embodiment, the fluid ejectors activated by the drop-firing controller are either, a different subgroup of fluid ejectors on the fluid ejection cartridge used to dispense the bioactive fluid, or a different fluid ejection cartridge.

Figure 6C:
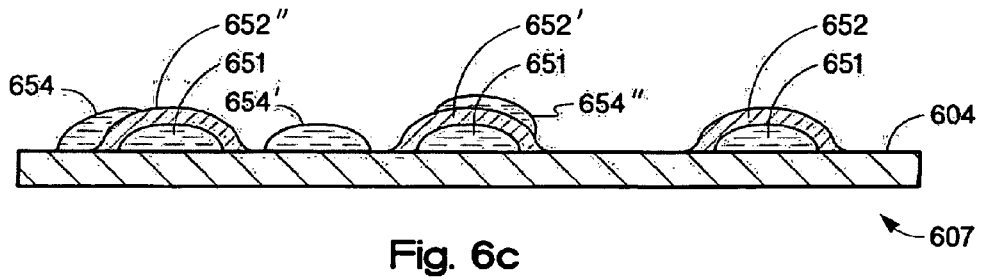
FIG. 6c is a cross-sectional view of a method for generating a dosage according to an alternate embodiment of this invention.

An alternate embodiment of the present invention where the process used for generating a dosage form includes ingestible ink deposited over the bioactive fluid is shown in a cross-sectional view in FIG. 6c. In this embodiment, after the bioactive fluid and the barrier material has been deposited onto the surface of the ingestible sheet 604, as described above, the drop-firing controller activates one and, typically, a plurality of ink ejectors, to eject fluid drops of an ingestible ink at various locations on the ingestible sheet 604 to form dots 654, 654' and 654". The dots 654, 654' and 654" are deposited in patterns using dot matrix manipulation or other means to generate an image, alphanumeric characters, or a machine understood code such as a one or two dimensional bar code, on the ingestible sheet 604. The dots 654, 654' and 654", the barrier deposits 652, 652", and 652" and deposits 651, 651', and 651" of the bioactive fluid on the ingestible sheet 604 form dosage form 607.

Figure 6D:
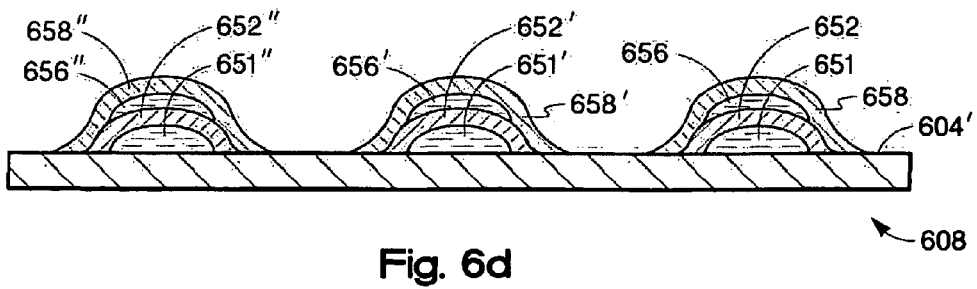
FIG. 6d is a cross-sectional view of a method for generating a dosage according to an alternate embodiment of this invention.

An alternate embodiment of the present invention where the process used for generating a dosage form includes deposition of more than one bioactive fluid onto the ingestible sheet 604' is shown in a cross-sectional view in FIG. 6d. In this embodiment, the deposits 651, 651', and 651" of the bioactive fluid and the deposits 652, 652' and 652" of the barrier material have been formed on the ingestible sheet 604' as described above. Next, the drop-firing controller activates one and, typically, a plurality of fluid ejectors, to eject fluid drops of a second bioactive fluid on the ingestible sheet 604' to form deposits 656, 656' and 656". In this embodiment, the fluid ejectors activated by the drop-firing controller to eject the second bioactive fluid are either, a different subgroup of fluid ejectors on the fluid ejection cartridge used to dispense the first bioactive fluid, or a different fluid ejection cartridge.

After the second bioactive fluid has been dispensed, a second barrier is then formed over the deposits 656, 656' and 656" forming barrier deposits 658, 658' and 658" forming dosage form 608. Preferably the second barrier material is the same as the first, however, depending on the properties and compatibilities of the first and second bioactive fluids as well as the first barrier material the second barrier material may be different from the first barrier material. Although FIG. 6d depicts two different bioactive fluids deposited on the ingestible sheet, more than two bioactive fluids can be deposited on an ingestible sheet.

FIGS. 6a-6d depict isolated deposits of the bioactive fluid and barrier material being deposited onto the ingestible sheet; however, by depositing overlapping deposits of, either or both, the bioactive fluid and barrier material layers of each material can be formed. In addition, the order of deposition can also be varied depending on the particular application. For example, the ingestible ink can be deposited before the bioactive fluid and the barrier material. Further, the ingestible sheet 604 or 604' shown in FIGS. 6a-6d can have, either or both, a releasable backing (not shown) or barrier material (not shown) coated on the surface opposite to the surface on which the bioactive fluid is dispensed.

Figure 7A:
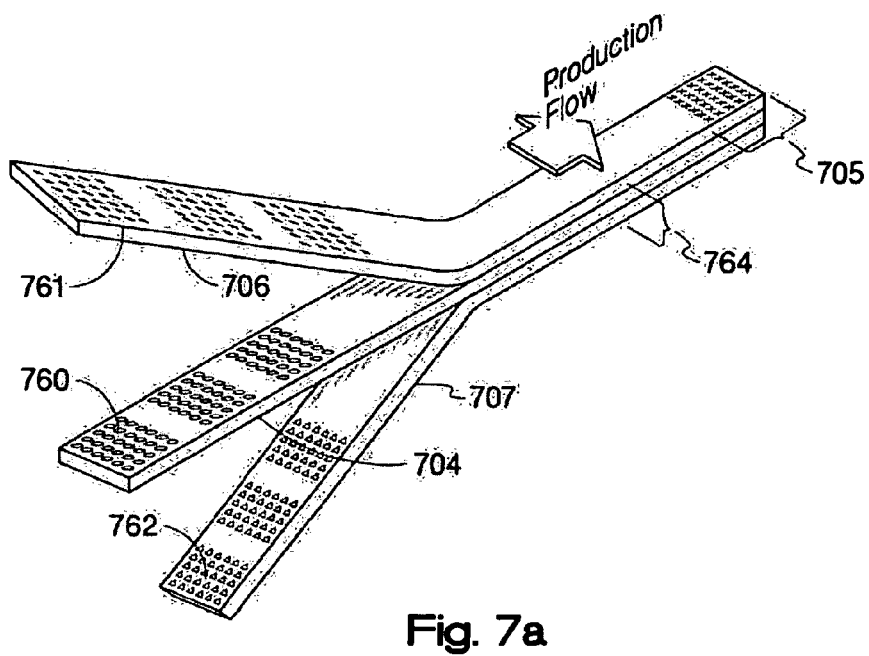
FIG. 7a is a perspective view of a process for manufacturing a dosage form according to an alternate embodiment of this invention.

An alternate embodiment of the present invention of a process for manufacturing a dosage form containing more than one bioactive fluid is shown in a perspective view in FIG. 7a. In this embodiment, multiple ingestible sheets 704, 706, and 707 each having multiple portions 760, 761, 762 respectively that have a bioactive fluid deposited thereon. The center ingestible sheet 704 is then sandwiched between the outer sheets 706 and 707 to form a laminated structure 764 where each of the multiple portions 760, 761, 762 are positioned where the portion 761 is above the portion 760 which is above the portion 762. This arrangement forms a dosage form 705 that contains multiple bioactive fluids.

Figure 7B:
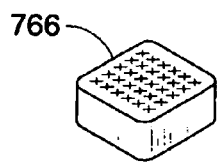
FIG. 7b is a perspective view of an encapsulated and unitized single dose according to an embodiment of this invention.

Although FIG. 7a depicts three layers of ingestible sheet being laminated, laminated structures containing two or more layers can be utilized. The ingestible sheets 704, 706, and 707 can be formed from the same or different materials. In addition, the various processes and resultant structures depicted in FIGS. 6a-6b can also be utilized. Further, other films such as a barrier film or ingestible adhesive film can also be laminated or coated on the different ingestible sheets 704, 706, and 707 to improve various properties such as water vapor transmission rate or adhesion depending on the particular bioactive fluids and the particular ingestible sheets being utilized. Subsequent to the lamination process the laminated structure 764 can further be encapsulated and unitized to form single dose 766 as shown in perspective view in FIG. 7b.

Figure 7C:
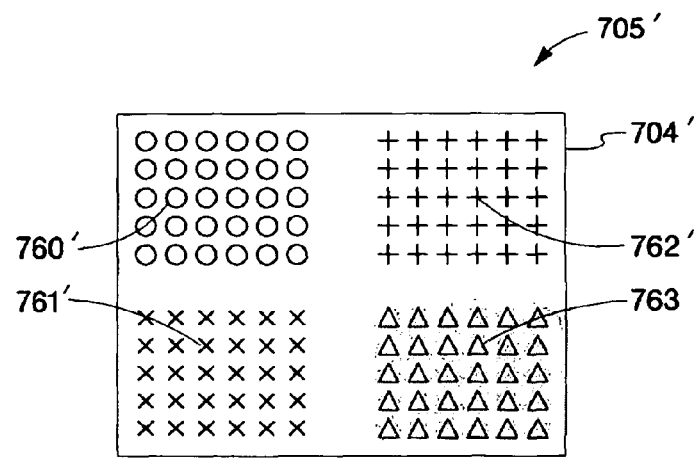
FIG. 7c is a plan view of a process for manufacturing a dosage form according to an alternate embodiment of this invention.

An alternate embodiment of the present invention of a process for manufacturing a dosage form containing more than one bioactive fluid is shown in a plan view in FIG. 7c. In this embodiment, an ingestible sheet 704' contains multiple portions 760', 761', 762', and 763 each containing a different bioactive fluid deposited thereon. The four multiple portions form a dosage form 705' that contains multiple bioactive fluids. Although FIG. 7c depicts four multiple portions, the ingestible sheet 704' containing two or more multiple portions can be utilized. The various processes and resultant structures depicted in FIGS. 6a-6b can also be utilized in this embodiment. In addition, other films such as a barrier film or ingestible adhesive film can also be laminated or coated on the ingestible sheet 704' to improve various properties such as water vapor transmission rate, acid resistance, or drug release rate depending on the particular bioactive fluids and the particular ingestible sheet being utilized. Further the multiple portions 760', 761', 762' and 763 can also be utilized in the laminated structure 764 shown in FIG. 7a by either making a larger dosage form or by folding.

Figure 8A:
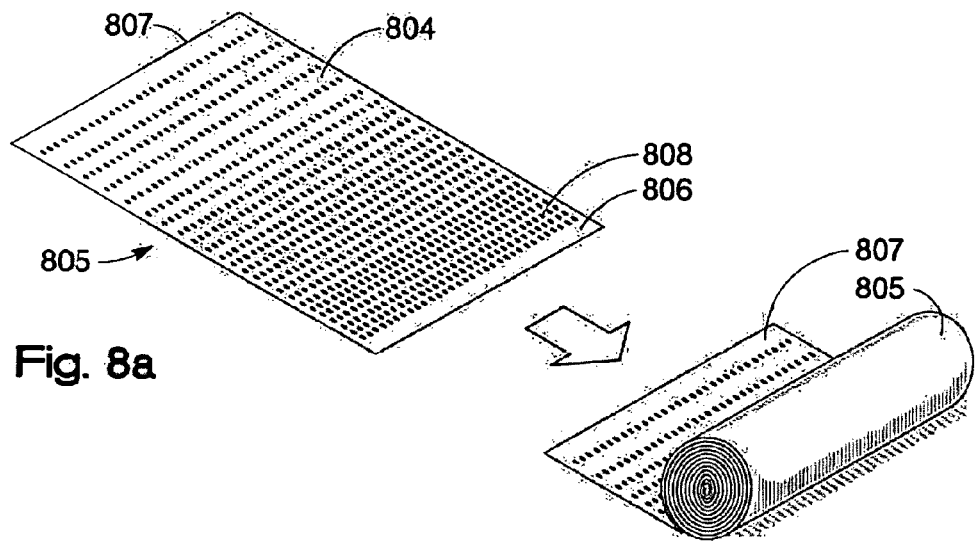
FIG. 8a is a perspective view of a dosage form to vary the amount of the bioactive fluid released over time according to an embodiment of this invention.
Figure 8B:
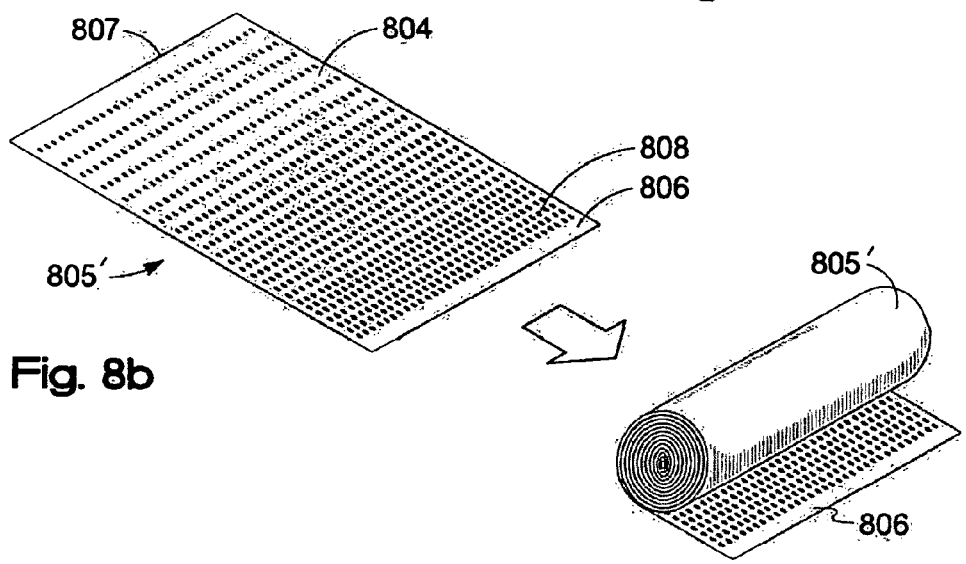
FIG. 8b is a perspective view of a dosage form to vary the amount of the bioactive fluid released over time according to a first alternate embodiment of this invention.
Figure 8C:
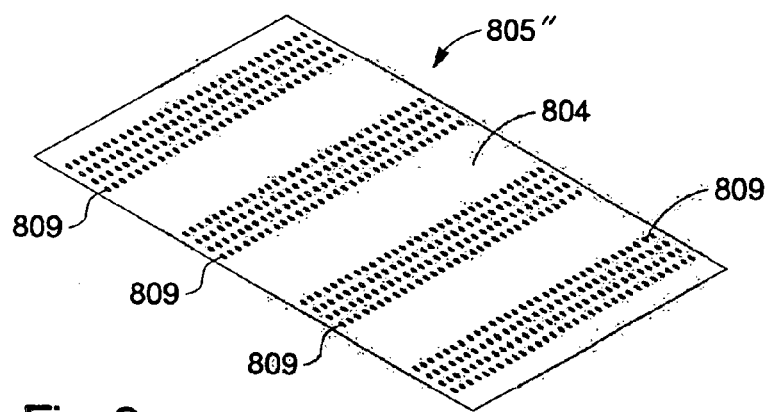
FIG. 8c is a perspective view of a dosage form to vary the amount of the bioactive fluid released over time according to a second alternate embodiment of this invention.

As noted above an expandable foam may be desirable for the rapid release of a bioactive fluid once ingested, however, some applications may want to vary the amount of the bioactive fluid released over time. An advantage of the present invention is the ability to make dosage forms that can vary the amount of bioactive fluid or drug released over time as shown in FIG. 8a-8c. In an alternate embodiment, shown in FIG. 8a, a fluid ejection cartridge (not shown) containing at least a bioactive fluid ejects the bioactive fluid onto an ingestible sheet 804 to form deposits 808 of the bioactive fluid dispensed in a two dimensional array over the surface of the ingestible sheet 804. In this embodiment, a dosage form 805 contains a first edge 806 having a greater density of the deposits 808 than a second edge 807 where the density of the deposits 808 between the first edge 806 and second edge 807 varies, forming a gradient of the bioactive fluid dispensed on the ingestible sheet. Although as shown in FIG. 8a the bioactive fluid is dispensed in the form of deposits 808 over the entire surface of dosage form 805 other forms can also be utilized such as centering the two dimensional array of deposits 808 in a narrower strip in the center of the dosage form 805 running from the edge 806 to the edge 807. The dosage form 805 is wound into a coil, where the edge 806 having the higher dot density forms the edge contained in the center of the coil and the edge 807 having the lower dot density forms the outer edge of the coil.

As the ingestible sheet 804 dissolves the radius of the coiled dosage form 805 decreases, resulting in a smaller surface area, thus the amount of bioactive fluid released can be varied or maintained constant. For example as shown in FIG. 8a a gradient that increases as the surface area decreases can be used to maintain a constant or increasing release rate depending on the particular gradient used. Thus, in this example the bioactive fluid is deposited in a gradient adapted to provide a dosage form that, after being ingested, the amount of the bioactive fluid released increases over time. Further, the bioactive fluid can also be deposited in a gradient adapted to provide a dosage form that, after being ingested, the amount of the bioactive fluid released remains constant over time However, as shown in FIG. 8b, a dosage form 805' that is coiled in the opposite direction where the edge 807, having the lower dot density, forms the center of the coil and the edge 806, having the higher dot density, forms the exterior surface of the coil; generates a gradient that decreases as the surface area decreases. Such a dosage form can be used to decrease the release rate as a function of time creating a loading dose. Thus, in this example the bioactive fluid is deposited in a gradient adapted to provide a dosage form that, after being ingested, the amount of the bioactive fluid released decreases over time.

A perspective view of an alternate embodiment of the present invention where repeat dosages are formed is shown in FIG. 8c. In this embodiment a fluid ejection cartridge (not shown) containing at least one bioactive fluid ejects the bioactive fluid onto the ingestible sheet 804 to form the deposits 808 of the bioactive fluid dispensed in a two dimensional array over discrete portions 809 on the surface of the ingestible sheet 804. The dosage form 805" is wound into a coil where each of the discrete portions 809 will release the deposited bioactive fluid at different times depending on the thickness of the ingestible sheet 804, the rate of dissolution of the ingestible sheet 804 and the particular placement of each discrete portion 809 among other variables. This embodiment provides a dosage form where a discrete amount of the bioactive substance is released at either repeatable times or discrete amounts of the bioactive substance is released at different times. Although each of the alternative embodiments shown in FIGS. 8a-8c are described in terms of fixed dot size and varying the dot density, other methods can also be utilized such as varying the drop size and keeping the dot density constant. This ability to vary the dosage release rate over time is an advantage over a conventionally formed tablet, which would release less bioactive material as the diameter of the table decreases. Thus, the present invention provides a dosage form where the amount of bioactive substance released over time, increases, decreases, remains constant, is repeatable, or a discrete dose is released at different times.

Figure 9A:
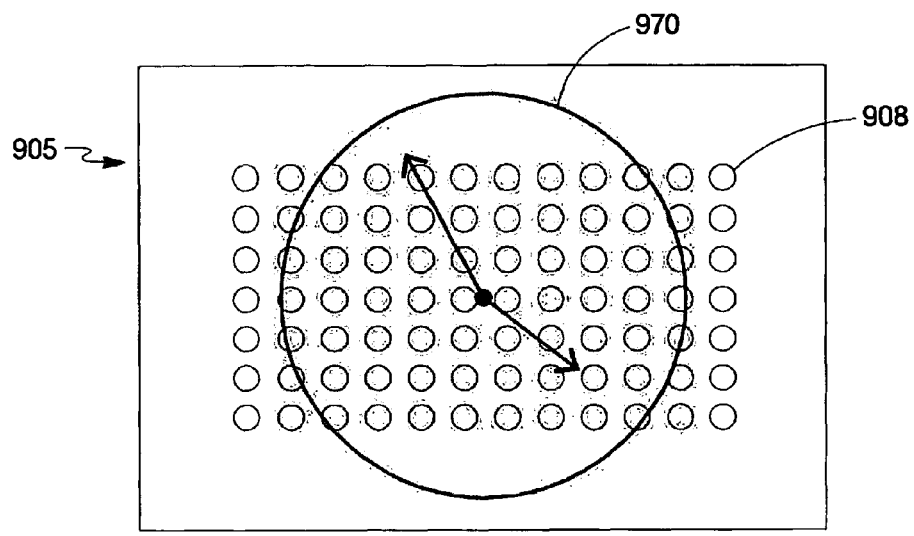
FIG. 9a is a plan view of a dosage form containing user information according to an embodiment of this invention.
Figure 9B:
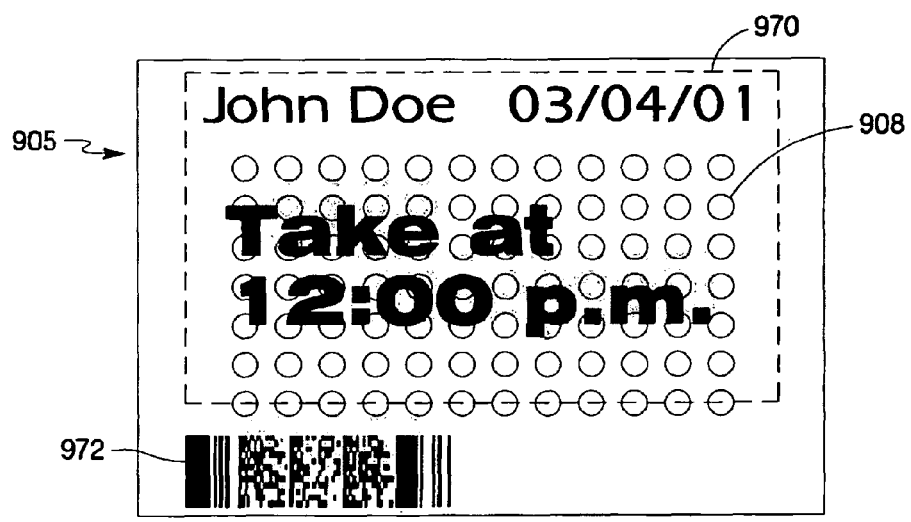
FIG. 9b is a plan view of a dosage form containing user information and manufacturing information according to an alternate embodiment of this invention.

Referring to FIGS. 9a-9b, an alternate embodiment of the present invention is shown where the dosage form 905 contains user information 970 to be conveyed to the user or patient. For example, FIG. 9a depicts the user information 970 as a clock showing the time the dose is to be taken or administered. In this particular example the user information 970 is deposited over the two dimensional array of the deposits 908 of the bioactive fluid. However, depending on the particular bioactive fluid and the particular ingestible sheet being utilized the bioactive fluid can also be deposited over the user information. Another example is shown in FIG. 9b where the information is a message indicating the name, date, and time to take the medicament. However, the user information 970 can be any symbol, icon, image, or text or combinations thereof, such as a company logo or cartoon character. Other examples of the type of information that can be conveyed to the user are the name of the medicament, the expiration date, the flavor of the ingestible sheet, or information having some marketing value. In addition, the dosage form 905 can also contain manufacturing information 972 to be used by the manufacturer and/or distributor. For example, FIG. 9b depicts the manufacturing information 972 as a two-dimensional bar code. The manufacturing information 972, however, can be any symbol, icon, image, or text or combinations thereof. Examples of various forms are a one-dimensional bar code, a text message, a code, or hologram. Examples of the various types of information that can be utilized in the manufacturing information 972 would be the composition of the ingestible sheet or results of quality control testing, data on compatibility with bioactive fluids, expiration dates, or part tracking information.

Figure 10A:
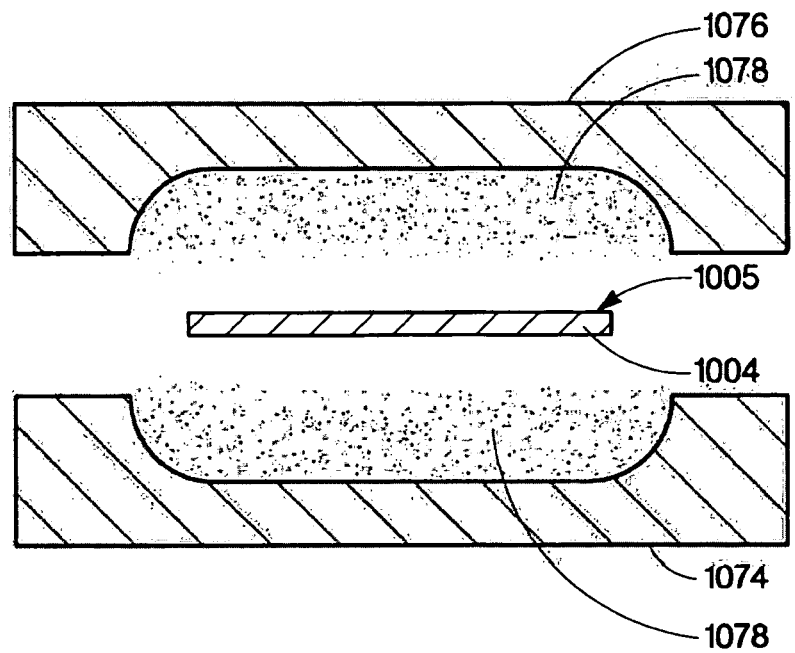
FIG. 10a is a cross-sectional view of a process for manufacturing a dosage form according to a third alternate embodiment of this invention.
Figure 10B:
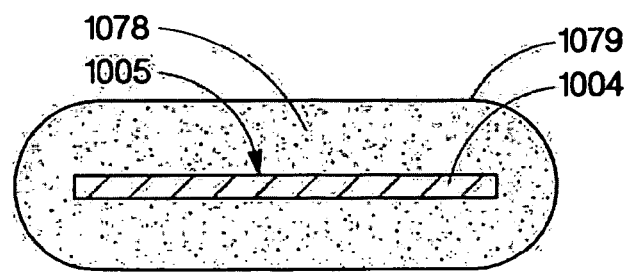

A cross-sectional view of an alternate embodiment of the present invention where a dosage form 1005 is encapsulated in a tablet 1079 is shown in FIG. 10b. In this embodiment, a lower die chamber 1074 and an upper die chamber 1076 are substantially filled with an excipient powder 1078 as shown in FIG. 10a. Dosage form 1005, which contains the bioactive fluid deposited on an ingestible sheet 1004, is positioned between the two die chambers such that the excipient powder formulation encases or encloses the dosage form 1005. Compressing the lower die chamber 1074 against the upper die chamber 1076 forms the tablet 1079. Preferably, the tablet is cylindrical with convex outer surfaces typically about 5 to 15 mm. in diameter and about 5 mm. in thickness. However, a variety of regular and irregular shapes and sizes can be utilized, such as ellipsoids, cuboids, indentations, polygonoids and other convex and concave surfaces. Optional subsequent processes including dedusting, drying, and coating may be performed.

Depending on the desired pharmacokinetic characteristics of the bioactive fluid dispensed on the ingestible sheet 1004, the excipient formulation may be similar to the ingestible sheet 1004 or one may select excipients that are dissimilar to the ingestible sheet to obtain tabletting or pharmacokinetic characteristics unlike the ingestible sheet 1004. For example microcrystalline sugar (97% sucrose and 3% maltodextrin) or cellulose, calcium phosphate, and sodium carboxymethylcellulose can be used with a cellulosic-based ingestible sheet. Sugars and corn, wheat, or rice starches can be used with starch-based ingestible sheets. Whereas silica added to improve flowability, stearates for lubrication, and guar gum or gelatin as binders are examples of dissimilar materials.

A preferable excipient formulation for direct compression tabletting of a dosage form made from an ingestible sheet which does not include the weight of the ingestible sheet nor the weight of the bioactive fluid dispensed is: about 70 weight percent lactose, about 25 weight percent microcrystalline cellulose, about 2 weight percent di-calcium phosphate dihydrate, 2 weight percent sodium carboxymethylcellulose, about 0.3 weight percent fumed silica and about 0.5 weight percent magnesium stearate. However, excipient ranges in formulations for direct compression tabletting of a dosage form made from an ingestible sheet which does not include the weight of the ingestible sheet nor the weight of the bioactive fluid dispensed are 0 to about 80 weight percent sugar, 0 to about 25 weight percent microcyrstalline cellulose, 0 to about 90 weight percent calcium phosphate, about 5 to about 25 weight percent starch, about 1 to about 2 weight percent sodium carboxymethylcellulose, about 0.2 to about 0.3 weight percent silica and about 0.5 to about 1 weight percent magnesium stearate can also be utilized.

In addition to improve adhesion between the excipient powder formulation and the ingestible sheet the excipient formulation can be modified by adding natural or synthetic polymers such as proteins, carboxymethylcellulose, polyvinylacetate, gelatins, or dextrins can be utilized to improve the adhesive properties of the excipient powder. It is also contemplated that an ingestible adhesive can be dispensed between the two die chambers prior to applying pressure to form the tablet. For example, a monomeric methyl or ethyl-cyanoacrylate type adhesive can be utilized. Alternatively, the ingestible sheet 1004 of the dosage form 1005 can be perforated to allow greater contact area between excipient powder 1078 contained in the upper die chamber 1076 and the lower die chamber 1074 or the dosage form 1005 can be formed in the shape of a ring containing an area in the center of the dosage form 1005 that allows the excipient powder in the two chambers to bond.

The process described above for compression tabletting of an ingestible sheet containing a bioactive fluid is advantageous over conventional tabletting in that the number of mixing steps can be reduced as well as the need to assure thorough mixing of the excipient with the pharmaceutical material to ensure proper dilution. In addition, flowability and drying criteria of the excipient formulation can also be relaxed.

Figure 11:
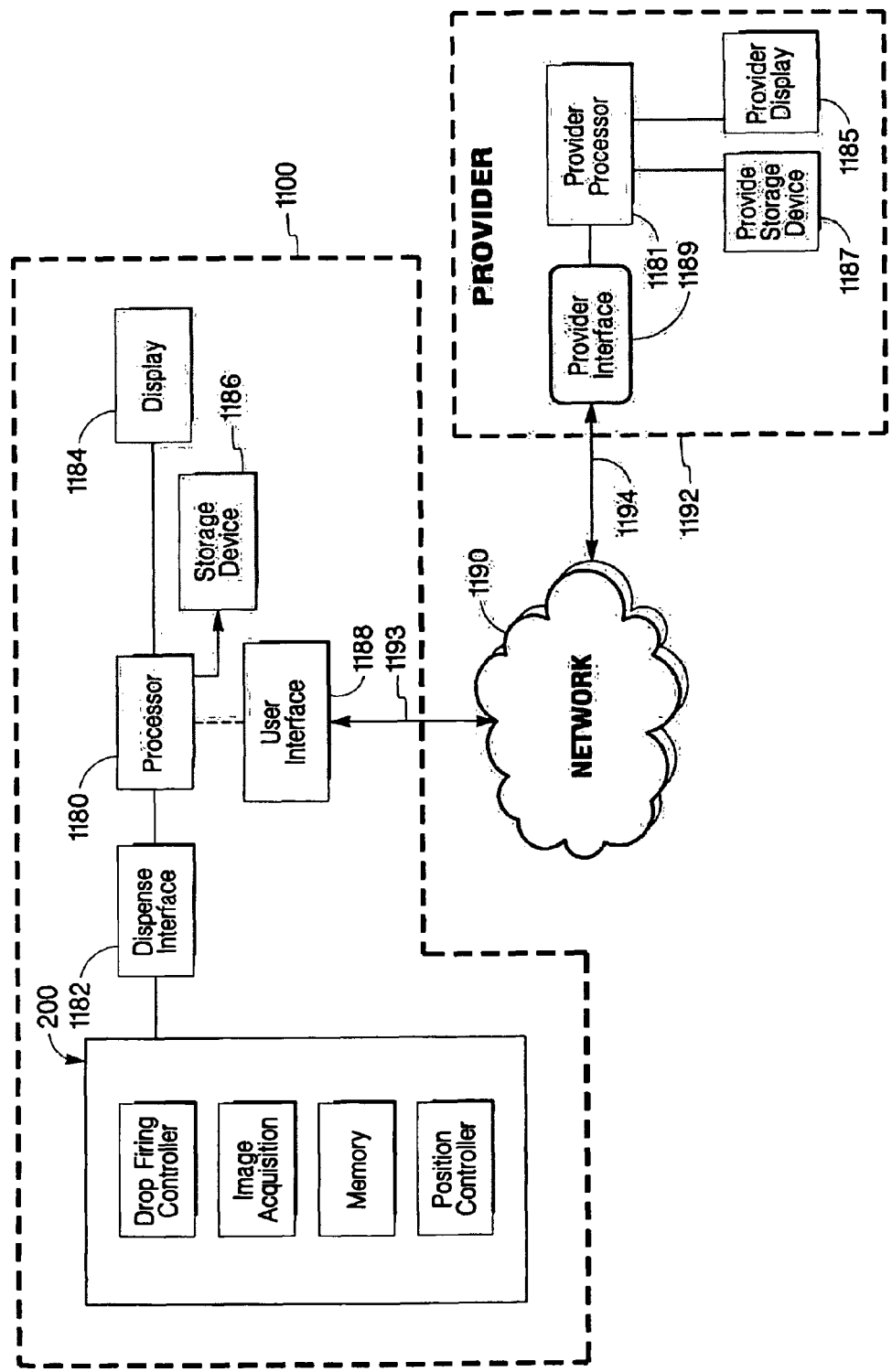
FIG. 11 is a block diagram of a bioactive fluid dispensing system for the interactive dispensing of a bioactive fluid on an ingestible sheet according to an embodiment of this invention.

An exemplary system 1100 for the interactive dispensing of a bioactive fluid on an ingestible sheet is shown as a schematic diagram in FIG. 11. In this embodiment a processor 1180 is coupled to a drop-firing controller via dispense interface 1182. The processor 1180 converts a specified quantity of the bioactive fluid to be dispensed into a number of drops or ejections to be activated by the drop-firing controller. This number is transmitted via the dispense interface 1182 to the drop-firing controller of the bioactive fluid dispensing system 200. The specified quantity of the bioactive fluid is then ejected onto the ingestible sheet forming a dosage form. The system 1100 also includes a storage device 1186 and a display device 1184 coupled to the processor 1180 to store and display information. For example user input information, system parameters, information and parameters associated the ingestible sheet can all be stored on storage device 1186 and/or displayed on display device 1184.

The system 1100 having the processor 1180, display device 1184, and storage device 1186 is advantageous over current methods of forming pharmaceutical doses in that it allows a user such as a doctor or pharmacist to generate variable doses as well as custom doses in the convenience of a hospital, pharmacy, or home environment. Further, such a system can also be utilized as a point of sale machine, in such locations as a pharmacy or a supermarket, to allow customers to create variable or custom doses of vitamins, nutritional supplements, or other over-the-counter medications.

In addition, the system 1100 also includes a user interface 1188 or signal receiver that is coupled to the processor 1180 and is also coupled via communication channel 1193 to an external communication network 1190 as shown in FIG. 11. Preferably, the external communication 1190 is a digital network such as what is commonly referred to as the Internet. Other communication channels such as wireless communication, wireline telephone, digital cable television, as well as other point-to-point, point-to-multipoint, and broadcast communications methods can also be used. The user interface or signal receiver 1188 receives a signal from a remote signal source specifying information to be utilized by system 1100. For example, the remote signal source can specify the quantity of bioactive fluid to be dispensed or an authorization code verifying the authority of the user to dispense the bioactive fluid. As shown in FIG. 11, the system 1100 can also be coupled to a provider system 1192 via network 1190.

The provider system 1192 includes a provider processor 1181, coupled to a provider display 1185, a provider storage device 1187, and a provider interface 1189. The provider interface 1189 is coupled via provider channel 1194 to the external communication network 1190. The provider system 1192 is utilized, for example, by a health care provider such as a doctor, a pharmacist, a nurse, appropriate insurance personnel, or other appropriate health care professional. Although FIG. 11 shows a single provider coupled to the system 1100 it also preferable to have multiple providers, such as doctors, pharmacists, nurses, insurance providers, and pharmaceutical manufacturers all coupled to the system 1100 over the external network 1190. This is particularly advantageous where system 1100 is located in a home where the patient can request information on the bioactive fluid and appropriate dosage information from a pharmacist, request information on the ingestible sheet from the manufacturer, and current health information from a doctor or nurse over the network; to form the appropriate pharmaceutical dose for that time or multiple doses to cover a period of the next day to several days or weeks. Such a system also allows potentially adverse drug interactions and individual allergies or intolerances and sensitivities to be flagged.

Figure 12:
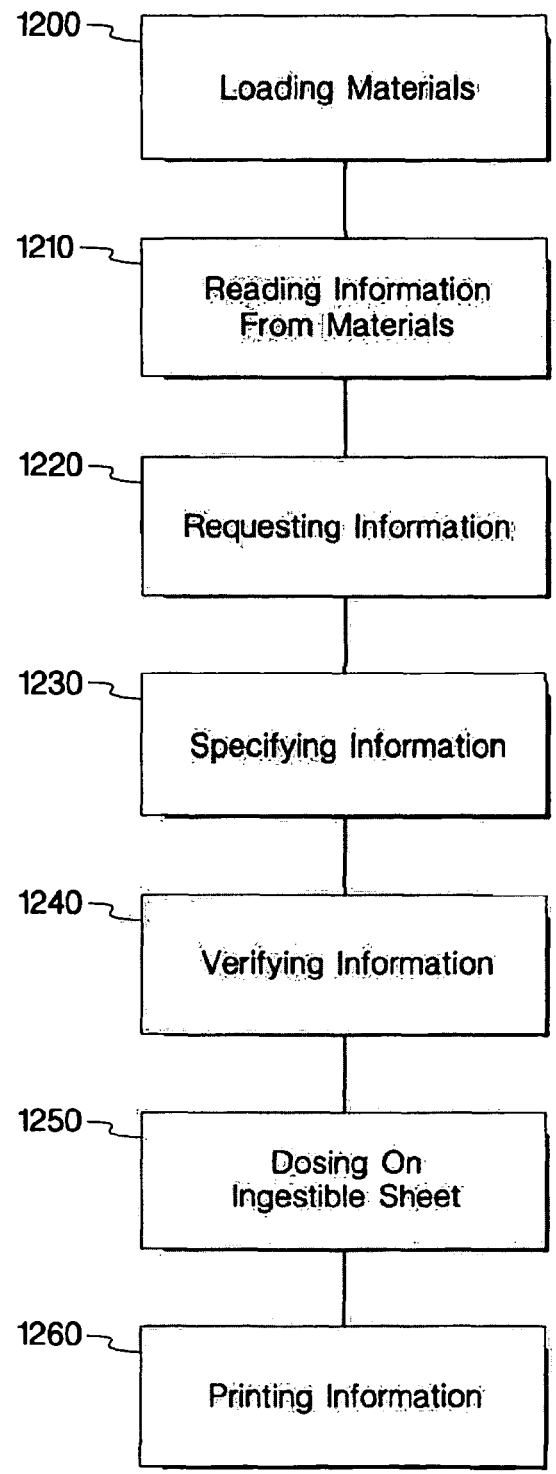
FIG. 12 is a flow diagram of an interactive method for generating a dosage form according to an embodiment of this invention.

An exemplary embodiment of an interactive method for generating a dosage form where the bioactive fluid is dispensed onto the ingestible sheet is shown as flow diagrams in FIGS. 12-13. An overview of the method is shown in FIG. 12. In step 1200, the various materials such as the bioactive fluid and the ingestible sheet are loaded or inserted into a bioactive fluid dispensing system. In Step 1210, information indicative of the materials is read either by the system or by a user who then manually enters the information into the system, such as the composition of the ingestible sheet and the active ingredients of the bioactive fluid. In step 1220, various forms of information are requested by the system such as requesting from the doctor or pharmacist the quantity or dose of the bioactive fluid to be dispensed. In step 1230, various forms of information are specified and then transmitted and received by the system, such as the doctor or pharmacist specifying the quantity or dose of the bioactive fluid to be dispensed. Various forms of information are verified in step 1240 such as verifying that the dose is within the correct range. The bioactive fluids as well as other materials such as the barrier material are dispensed on the ingestible sheet in step 1250 providing all of verification steps were successfully completed. In optional step 1260, appropriate user and manufacturing information is printed on the ingestible sheet.

Figure 13A:
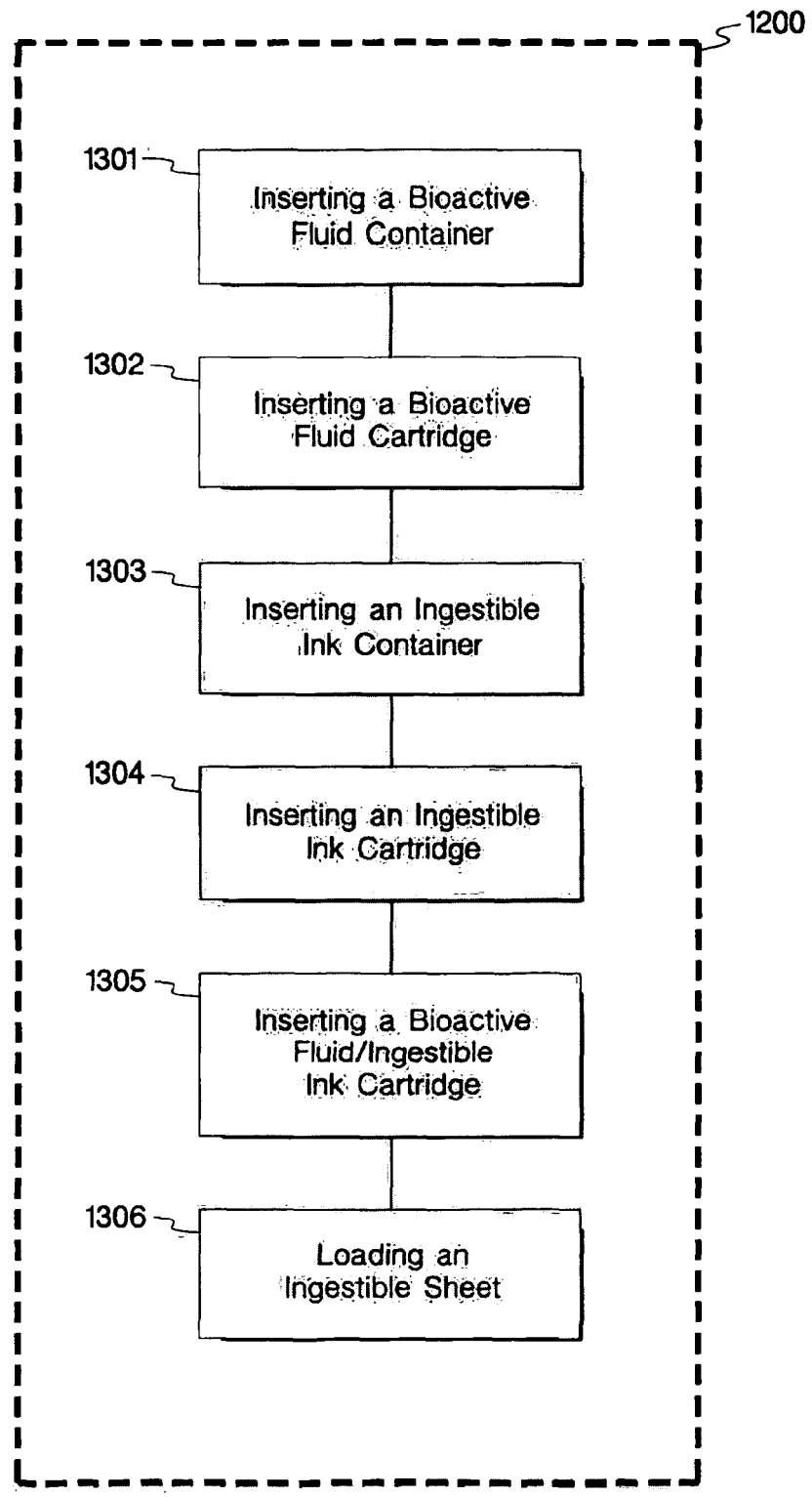
FIG. 13a is a flow diagram showing a more detailed view of the steps for loading materials shown in FIG. 12.

A more detailed view of the various steps associated with the loading step 1200 is shown in FIG. 13a. In step 1301, an off-axis bioactive fluid container is inserted into the dispensing system where the container, after insertion is fluidically coupled to a bioactive fluid reservoir of a semi-permanent cartridge. Either a replaceable or semi-permanent bioactive fluid ejection cartridge is inserted in the dispensing system in step 1302. An off-axis ingestible ink container, and either a replaceable or semi-permanent ingestible ink ejection cartridge, are inserted into the dispensing system in steps 1303 and 1304 respectively, where the off-axis ink container is fluidically coupled to an ink reservoir in a semi-permanent ink cartridge. Depending on the particular ingestible sheet, and bioactive fluid utilized, a cartridge containing a mixture of the bioactive fluid and the ingestible ink can be inserted into the system in step 1305. In step 1306, an ingestible sheet is loaded into the dispensing system.

Figure 13B:
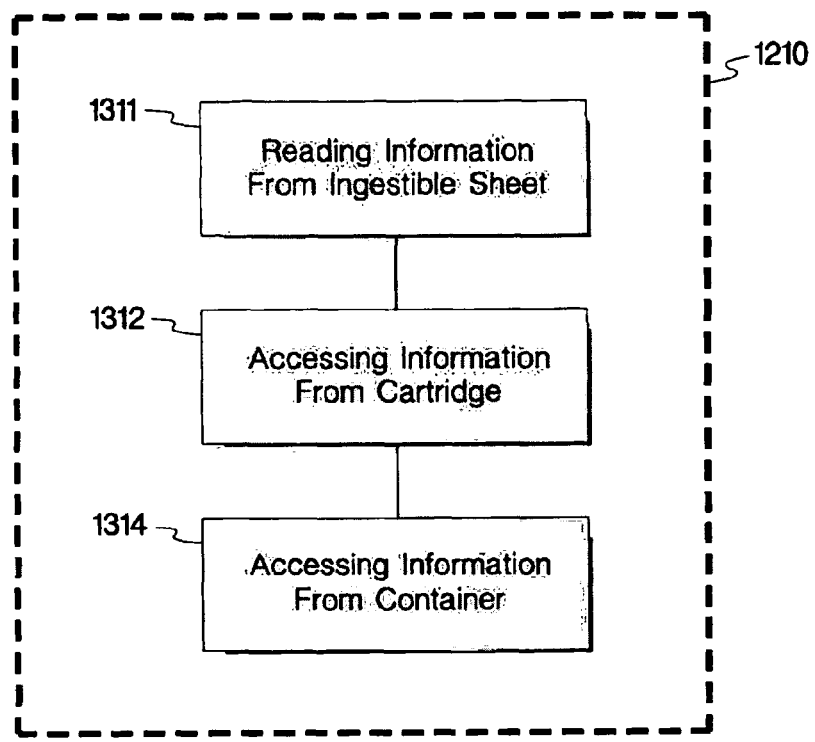
FIG. 13b is a flow diagram showing a more detailed view of the steps for reading information from materials shown in FIG. 12.

A more detailed view of the various steps associated with the reading step 1210 is shown as a flow diagram in FIG. 13b. In step 1311, information is read from the ingestible sheet. For example, the composition or the expiration date of the ingestible sheet can be read by the system utilizing an image acquisition system scanning a bar code. Preferably this information is stored in a machine readable form, however, a human perceptible form can also be utilized. In steps 1312 and 1314 information from the bioactive fluid cartridge and from the bioactive fluid container is accessed or read respectively. Preferably this information is stored in a memory chip that this accessed, however, other means can also be utilized such as printing the information on the cartridge in a machine readable or human perceptible form.

Figure 13C:
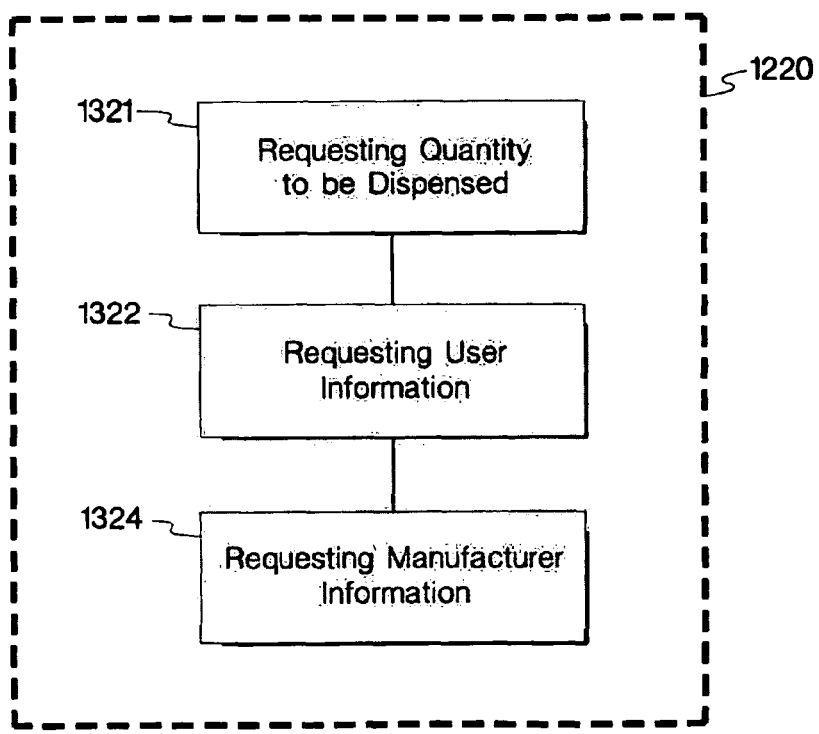
FIG. 13c is a flow diagram showing a more detailed view of the steps for requesting information shown in FIG. 12.

A more detailed view of the various steps associated with the requesting step 1220 is shown as a flow diagram in FIG. 13c. In step 1321 the quantity of the bioactive fluid to be dispensed is requested by the bioactive fluid dispensing system. For example, this could be displayed on a display device located in the vicinity of the dispensing system or it can be displayed on a remote display device such a doctor's or pharmacist's office. User information is requested by the system in step 1322. This information is any information about the user, i.e. typically the patient, that can be utilized for example in determining the appropriate dose, such as the patient's height, weight, age, etc. or information that is used by the user in administering the dosage form. In step 1324, manufacturer's information is requested by the system. This information is any information from the manufacturer of the bioactive fluid and/or the ingestible sheet. For example, this information can be the same or similar to that obtained in steps 1311, 1312, 1314 and can be used in conjunction with that information to act as a verification.

Figure 13D:
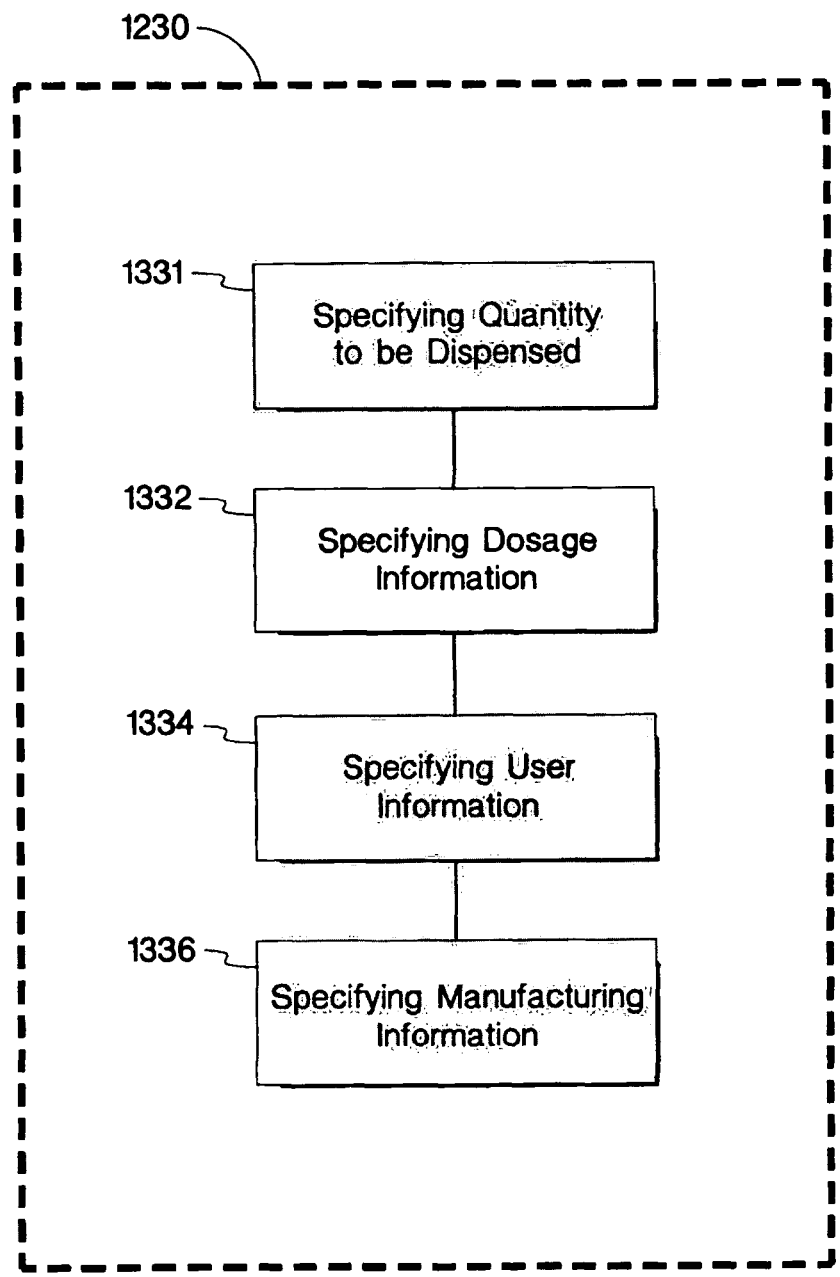
FIG. 13d is a flow diagram showing a more detailed view of the steps for specifying information shown in FIG. 12.

A more detailed view of the various steps associated with the specifying step 1230 is shown as a flow diagram in FIG. 13d. In step 1331, the quantity of the bioactive fluid to be dispensed is specified, for example by a doctor or pharmacist, transmitted to and received by the bioactive fluid dispensing system. In step 1332, dosage information, such as dosage forms that vary the amount of bioactive fluid released over time as shown in FIG. 8, is specified, transmitted to and received by the system. User information is specified transmitted to and received by the system in step 1334. This information is any information about the user, i.e. typically the patient, that can be utilized for example in determining the appropriate dose, such as the patient's height, weight, age, etc. or information that is used by the user in administering the dosage form. In step 1336, manufacturer's information is specified. This information is any information from the manufacturer of the bioactive fluid and/or the ingestible sheet. For example, this information can be the same or similar to that obtained in steps 1311, 1312, 1314 and can be used in conjunction with that information to act as a verification.

Figure 13E:
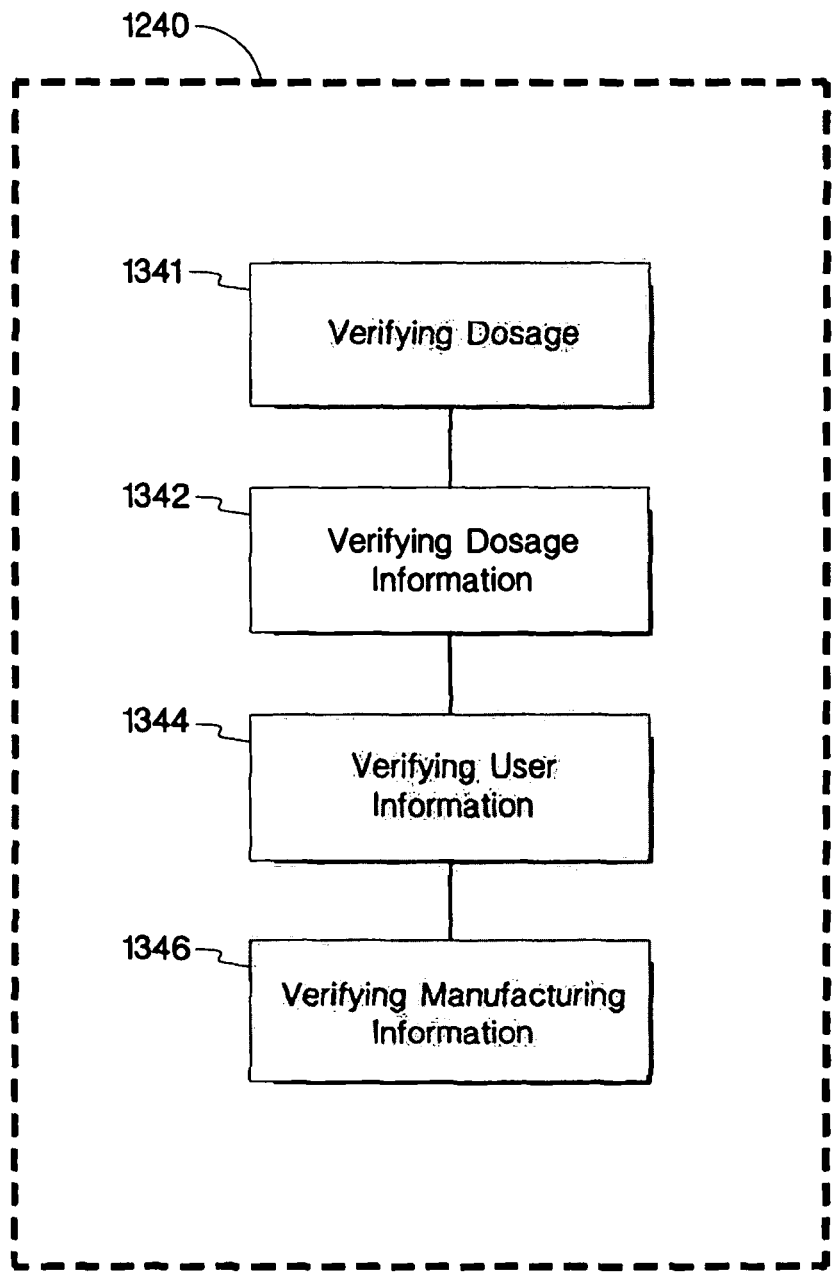
FIG. 13e is a flow diagram showing a more detailed view of the steps for verifying information shown in FIG. 12.

A more detailed view of the various steps associated with the verifying step 1240 is shown as a flow diagram in FIG. 13e. In step 1341, the dosage quantity is verified. Step 1341 verifies information obtained in a previous step such as step 1331 or multiple steps is used to verify the dosage specified, is either correct or within an acceptable range. For example, the information accessed from the bioactive fluid cartridge in step 1312 is compared to the specified quantity to be dispensed in step 1331. Another example would be the use of a third party authorization key where the dosage quantity is verified utilizing the key that is located on the user's system or is accessed via a network such as the Internet. The dosage information specified in step 1332 is verified in step 1342. For example, if the information has been previously entered then the information specified in step 1332 can be verified from stored information stored on a storage device. However, if step 1332 is being performed for the first time with a given user then either the information can be retransmitted back to the person specifying or the information can be verified by a third party such as a doctor or an insurance agent via a network such as the Internet. In step 1344, user information is verified. This step can also be carried out using either previously stored information or a third party as described above in step 1342. The manufacturer's information is verified in step 1346. This step can also be carried out using either previously stored information or a third party as described above in step 1342. The manufacturer's information is any information from the manufacturer of the bioactive fluid or the ingestible sheet obtained in steps 1336 or step 1210.

Figure 13F:
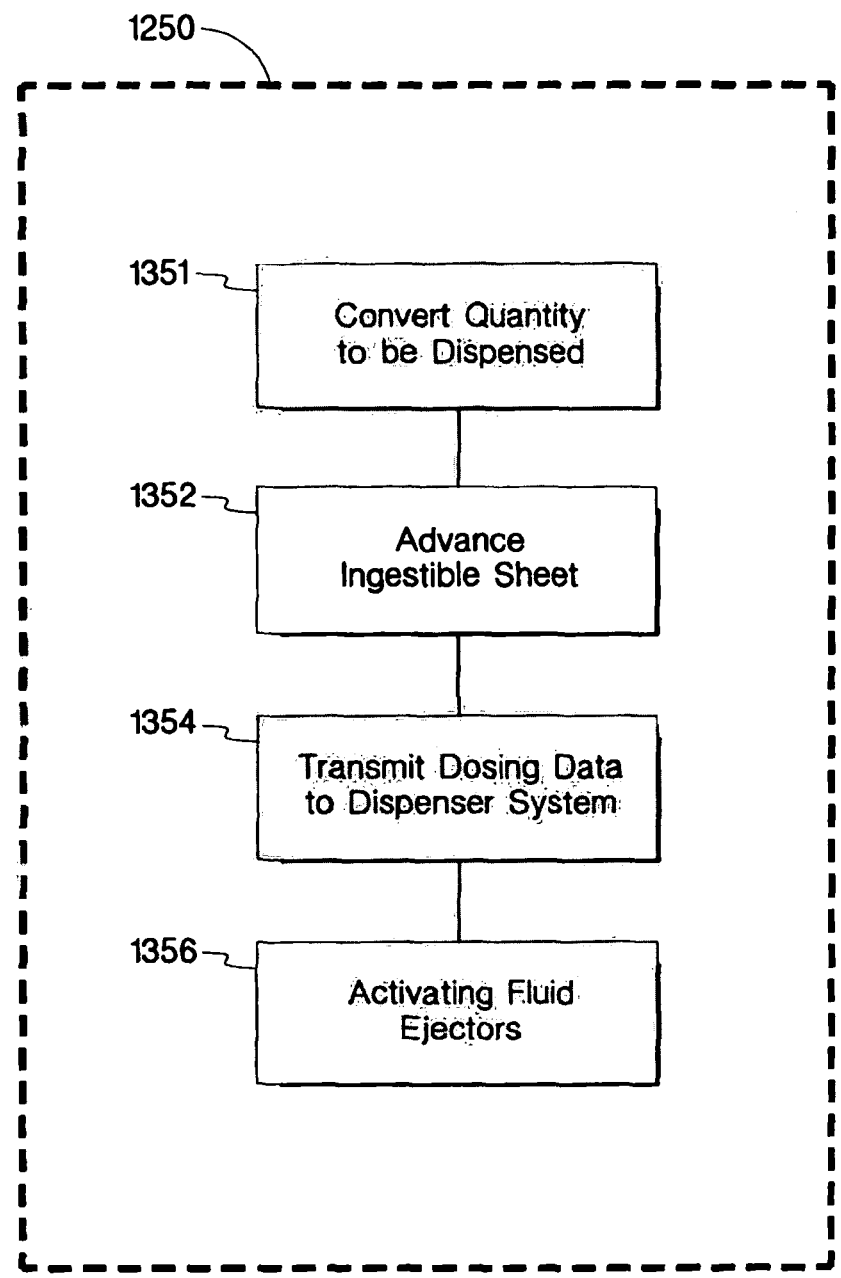
FIG. 13f is a flow diagram showing a more detailed view of the steps dosing the bioactive fluid on the ingestible sheet shown in FIG. 12.

A more detailed view of the various steps associated with dosing of the bioactive fluid on the ingestible sheet in step 1250 is shown as a flow diagram in FIG. 13f provided the verification steps described above have been successfully completed. In step 1351, the quantity of bioactive fluid to be dispensed is converted on a processor into a number of activations of a fluid ejector. The ingestible sheet is advanced into a fluid ejection area beneath the ejector head or heads in step 1352. The dosing data preferably in the form of the number of activations of a fluid ejector is transmitted from the processor to the dispense system in step 1354. In step 1356, the fluid ejectors are activated to produce the pharmaceutical dose. Preferably, the drops are ejected in a predetermined fluid swath pattern using dot matrix manipulation, forming the pharmaceutical dose from the cartridge containing the bioactive fluid, however other processes of firing the fluid ejectors can also be utilized. In addition, a custom bioactive fluid dose can also be generated by inputting the user information, the manufacturing information, dosage information, as well as appropriate information from the bioactive fluid cartridge into a dose algorithm. The dose algorithm then combines this information in a predetermined manner to generate a custom bioactive fluid dose.

Figure 13G:
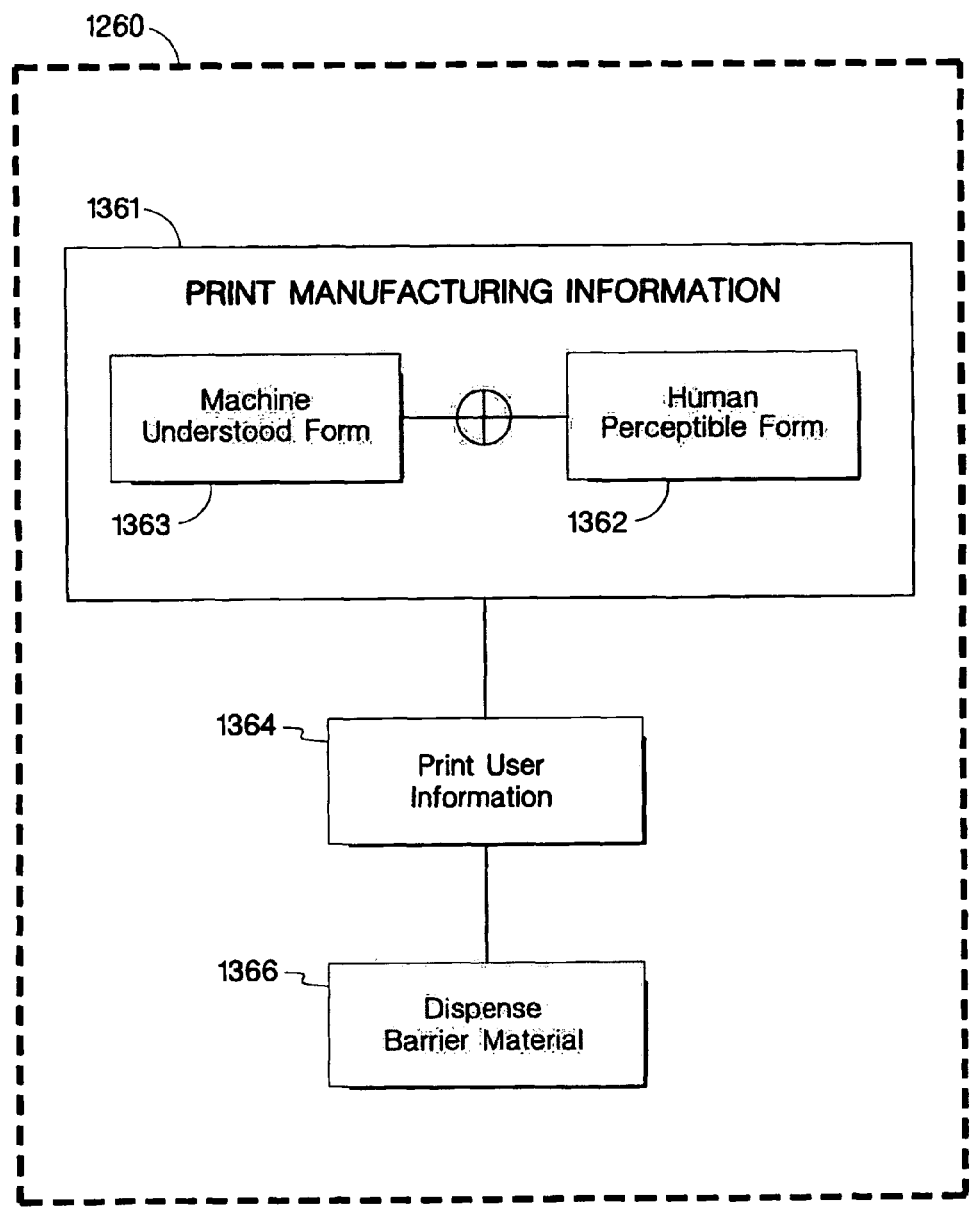
FIG. 13g is a flow diagram showing a more detailed view of the steps printing information shown in FIG. 12.

A more detailed view of the various steps associated with printing information on the ingestible sheet, in step 1260, is shown as a flow diagram in FIG. 13g. In step 1361, appropriate manufacturing information, such as the composition of the ingestible sheet and the name or the bioactive composition, is printed on the ingestible sheet. The manufacturing information printed in step 1361 can be printed either in a machine understood form in step 1363 or it can be printed in a human perceptible form in step 1362 or in some combination thereof. The user information, such as the name of the user or patient and the date and time for administering the dosage form, is printed on the ingestible sheet in step 1364. In step 1366, preferably the barrier material is dispensed over the bioactive fluid previously dispensed in step 1356. However, depending on the particular ingestible sheet, bioactive fluid, and dosage structure (e.g. capsule or laminated structure) being utilized, the barrier material may be dispensed before the bioactive fluid is dispensed.

The present invention can advantageously reduce the number of therapeutically inactive materials, the number of dilutions, and the number of mixings in the manufacture of unit dosage forms. In addition, the bioactive fluid cartridge and the bioactive fluid dispensing system of the present invention provides for the custom dispensing of pharmaceutical unit dosage forms where the type of pharmaceutical and the quantity of the selected drug can be easily varied to meet a specific prescription. The bioactive fluid cartridge and the bioactive fluid dispensing system of the present invention provides the ability of dispensing multiple, different pharmaceuticals in varied, selected quantities to a single receiving medium thus simplifying the taking of drugs, especially combinations of different drugs by providing multiple drugs in one dose.

What is claimed is:

1. A laminated structure including ingestible sheets usable in an apparatus for manufacturing a pharmaceutical dose, comprising:
 a first ingestible sheet having multiple portions, each of the first ingestible sheet multiple portions including a two dimensional array of deposits of a first bioactive fluid dispensed thereon;
 a second ingestible sheet laminated to the first ingestible sheet so that the second ingestible sheet covers the deposits of the first bioactive fluid, the second ingestible sheet having multiple portions that are respectively aligned with the multiple portions of the first ingestible sheet, each of the second ingestible sheet multiple portions including a two dimensional array of deposits of a second bioactive fluid dispensed thereon, the deposits of the second bioactive fluid being exposed and the second bioactive fluid being different from the first bioactive fluid; and
 a releasable backing that is peelable from a back surface of the first ingestible sheet;
 and wherein each of the respectively aligned multiple portions of the first and second ingestible sheets forms a single dosage form that contains multiple bioactive fluids.

2. The laminated structure of claim 1, wherein said first and second ingestible sheets further comprise a component selected from the group consisting of starch, glycerin, gelatin, cellulose, and polysaccharides.

3. The laminated structure of claim 1, wherein said first and second ingestible sheets contain a water expandable foam.

4. The laminated structure of claim 1, wherein said first and second ingestible sheets each has a thickness from about 10 microns to about 350 microns.

5. The laminated structure of claim 2, wherein said first and second ingestible sheets are pre-perforated sheets.

6. The laminated structure of claim 5, wherein said first and second ingestible sheets each contains a starch and glycerin-based paper.

7. The laminated structure of claim 1, wherein each of said first and second ingestible sheets further comprises a component selected from the group consisting of restructured fruits, restructured vegetables, and any combination thereof.

8. The laminated structure of claim 1, further comprising perforations that delineate the single dosage forms.

9. The laminated structure of claim 1 wherein each of the single dosage forms includes a separator around its peripheral edge.

10. The laminated structure of claim 1, further comprising an ingestible ink deposited on the second ingestible sheet in a pattern.

11. The laminated structure of claim 1 wherein the single dose forms are repeat dosages of one another.

12. The laminated structure of claim 1, further comprising a barrier material deposited under the first bioactive fluid, under the second bioactive fluid, or under both the first and second bioactive fluids.

13. The laminated structure of claim 1, further comprising an information portion of the second ingestible sheet having manufacturing information disposed thereon.

14. The laminated structure of claim 13, wherein said manufacturing information includes at least one item selected from the group consisting of, a date of manufacture, a composition of the ingestible sheet, an inspection date, an expiration date, quality control information, data on compatibility with bioactive fluids, and dispensing system parameters.

15. The laminated structure of claim 13, wherein said information portion has user information disposed thereon.

16. The laminated structure of claim 15, wherein said user information includes patient information.

* * * * *